United States Patent
Wong et al.

(10) Patent No.: US 8,242,099 B2
(45) Date of Patent: *Aug. 14, 2012

(54) IMPLANTS AND METHODS FOR TREATING INFLAMMATION-MEDIATED CONDITIONS OF THE EYE

(75) Inventors: Vernon G. Wong, Menlo Park, CA (US); Mae W. L. Hu, Los Altos Hills, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/271,451

(22) Filed: Oct. 12, 2011

(65) Prior Publication Data

US 2012/0035146 A1 Feb. 9, 2012

Related U.S. Application Data

(63) Continuation of application No. 12/646,522, filed on Dec. 23, 2009, now Pat. No. 8,063,031, which is a continuation of application No. 10/671,816, filed on Sep. 25, 2003, now abandoned, which is a continuation of application No. 09/693,008, filed on Oct. 20, 2000, now Pat. No. 6,726,918.

(60) Provisional application No. 60/216,236, filed on Jul. 5, 2000.

(51) Int. Cl.
| A61K 31/573 | (2006.01) |
| A61K 31/56  | (2006.01) |
| A61K 31/58  | (2006.01) |
| A61P 27/02  | (2006.01) |
| A61P 29/00  | (2006.01) |

(52) U.S. Cl. ......... 514/174; 514/169; 514/179; 514/180
(58) Field of Classification Search ..................... None
See application file for complete search history.

(56) References Cited

U.S. PATENT DOCUMENTS

| 3,416,530 A | 12/1968 | Ness |
| 3,432,592 A | 3/1969 | Speiser |
| 3,845,770 A | 11/1974 | Theeuwes et al. |
| 3,914,402 A | 10/1975 | Shell |
| 3,916,899 A | 11/1975 | Theeuwes et al. |
| 3,921,632 A | 11/1975 | Bardani |
| 3,961,628 A | 6/1976 | Arnold |
| 3,986,510 A | 10/1976 | Higuchi et al. |
| 4,008,864 A | 2/1977 | Torphammar et al. |
| 4,014,334 A | 3/1977 | Theeuwes et al. |
| 4,063,064 A | 12/1977 | Saunders et al. |
| 4,088,864 A | 5/1978 | Theeuwes et al. |
| 4,144,317 A | 3/1979 | Higuchi et al. |
| 4,180,646 A | 12/1979 | Choi et al. |
| 4,186,184 A | 1/1980 | Zaffaroni |
| 4,200,098 A | 4/1980 | Ayer et al. |
| 4,201,210 A | 5/1980 | Hughes et al. |
| 4,285,987 A | 8/1981 | Ayer et al. |
| 4,300,557 A | 11/1981 | Refojo et al. |
| 4,304,765 A | 12/1981 | Shell et al. |
| 4,327,725 A | 5/1982 | Cortese et al. |
| 4,402,979 A | 9/1983 | Shen et al. |
| 4,451,254 A | 5/1984 | Dinius et al. |
| 4,474,451 A | 10/1984 | Mizokami |
| 4,478,818 A | 10/1984 | Shell et al. |
| 4,494,274 A | 1/1985 | Thurlow |
| 4,521,210 A | 6/1985 | Wong |
| 4,599,353 A | 7/1986 | Bito |
| 4,668,506 A | 5/1987 | Bawa |
| 4,756,911 A | 7/1988 | Drost et al. |
| 4,801,460 A | 1/1989 | Goertz et al. |
| 4,806,337 A | 2/1989 | Snipes et al. |
| 4,853,224 A | 8/1989 | Wong |
| 4,863,457 A | 9/1989 | Lee |
| 4,865,846 A | 9/1989 | Kaufman |
| 4,945,089 A | 7/1990 | Clark |
| 4,959,217 A | 9/1990 | Sanders et al. |
| 4,966,849 A | 10/1990 | Vellee et al. |
| 4,997,652 A | 3/1991 | Wong |
| 5,004,601 A | 4/1991 | Snipes |
| 5,004,614 A | 4/1991 | Staniforth |
| 5,006,342 A | 4/1991 | Cleary et al. |
| 5,019,400 A | 5/1991 | Gombotz |
| 5,028,624 A | 7/1991 | Chan et al. |
| 5,034,413 A | 7/1991 | Chan et al. |
| 5,075,115 A | 12/1991 | Brine |

(Continued)

FOREIGN PATENT DOCUMENTS

CA    1333770    10/1988

(Continued)

OTHER PUBLICATIONS

U.S. Appl. No. 07/357,394, filed May 1989.
U.S. Appl. No. 07/386,835, filed Jul. 1989.
U.S. Appl. No. 10/820,563, filed Apr. 2004.
U.S. Appl. No. 60/587,092, filed Jul. 2004.
Ahmad, M., et al. "Ortho Ester Hydrolysis: Direct Evidence for a Three-Stage Reaction Mechanism," *Journal of American Chemistry*, 1979; 101(10):2669-2677.
Ahmed, I., et al. "Macular disorders: cystoid macular edema," *Ophthalmology*, Yanoff, M., Duker, J.S., eds. London: Mosby, 1999, 34.1-34.6.
Akduman, L., et al. "The early treatment diabetic retinopathy study," *Clinical trials in ophthalmology: a summary and practice guide*, Kertes, P.S., Conway, M.D., eds. Baltimore: Williams & Wilkins, 1998; 15-35.
American Academy of Ophthalmology; Basic and Clinical Science Course: Intraocular inflammation and Uveitis Section 9, 2003-2004 57-80, 102-103, 152-156.

(Continued)

*Primary Examiner* — Shanon A Foley
(74) *Attorney, Agent, or Firm* — Louis V. Wollenberger; Joel B. German; Debra D. Condino

(57) ABSTRACT

Methods for treating inflammation-mediated conditions of the eye are described, comprising: implanting into the vitreous of the eye of an individual a bioerodible implant comprising a steroidal anti-inflammatory agent and a bioerodible polymer, wherein the implant delivers the agent to the vitreous in an amount sufficient to reach a concentration equivalent to at least about 0.05 μg/ml dexamethasone within about 48 hours and maintains a concentration equivalent to at least about 0.03 μg/ml dexamethasone for at least about three weeks.

5 Claims, No Drawings

U.S. PATENT DOCUMENTS

| | | | |
|---|---|---|---|
| 5,082,655 A | 1/1992 | Snipes et al. |
| 5,164,188 A | 11/1992 | Wong |
| 5,169,638 A | 12/1992 | Dennis et al. |
| 5,268,178 A | 12/1993 | Calhoun et al. |
| 5,314,419 A | 5/1994 | Pelling |
| 5,322,691 A | 6/1994 | Darougar et al. |
| 5,330,992 A | 7/1994 | Eissenstat et al. |
| 5,356,629 A | 10/1994 | Sander et al. |
| 5,378,475 A | 1/1995 | Smith et al. |
| 5,384,333 A | 1/1995 | Davis et al. |
| 5,385,887 A | 1/1995 | Yim et al. |
| 5,443,505 A | 8/1995 | Wong |
| 5,476,511 A | 12/1995 | Gwon et al. |
| 5,501,856 A | 3/1996 | Ohtori et al. |
| 5,597,897 A | 1/1997 | Ron et al. |
| 5,601,844 A | 2/1997 | Kagayama et al. |
| 5,656,297 A | 8/1997 | Bernstein et al. |
| 5,660,847 A | 8/1997 | Magruder et al. |
| 5,660,851 A | 8/1997 | Domb |
| 5,688,819 A | 11/1997 | Woodward et al. |
| 5,693,335 A | 12/1997 | Xia et al. |
| 5,707,643 A | 1/1998 | Ogura |
| 5,755,785 A | 5/1998 | Rowsey et al. |
| 5,766,242 A | 6/1998 | Wong |
| 5,773,019 A | 6/1998 | Ashton et al. |
| 5,773,021 A | 6/1998 | Gurtler et al. |
| 5,824,072 A | 10/1998 | Wong |
| 5,824,074 A | 10/1998 | Koch |
| 5,869,079 A | 2/1999 | Wong |
| 5,882,682 A | 3/1999 | Rork et al. |
| 5,902,598 A | 5/1999 | Chen et al. |
| 5,941,250 A | 8/1999 | Aramant et al. |
| 5,962,027 A | 10/1999 | Hughes |
| 5,972,369 A | 10/1999 | Roorda et al. |
| 6,045,791 A | 4/2000 | Liu |
| 6,046,187 A | 4/2000 | Berde et al. |
| 6,051,576 A | 4/2000 | Ashton et al. |
| 6,063,116 A | 5/2000 | Kelleher |
| 6,074,661 A | 6/2000 | Olejnik et al. |
| 6,217,895 B1 | 4/2001 | Guo et al. |
| 6,217,911 B1 | 4/2001 | Vaugn et al. |
| 6,309,669 B1 | 10/2001 | Setterstrom et al. |
| 6,329,369 B1 | 12/2001 | Chow et al. |
| 6,331,313 B1 | 12/2001 | Wong et al. |
| 6,369,116 B1 | 4/2002 | Wong et al. |
| 6,403,649 B1 | 6/2002 | Woodward et al. |
| 6,497,729 B1 | 12/2002 | Moussy et al. |
| 6,534,542 B2 | 3/2003 | Chow et al. |
| 6,537,568 B2 | 3/2003 | Olejnik et al. |
| 6,545,182 B2 | 4/2003 | Chow et al. |
| 6,548,078 B2 | 4/2003 | Guo et al. |
| 6,699,493 B2 | 3/2004 | Wong |
| 6,713,081 B2 | 3/2004 | Robinson et al. |
| 6,726,918 B1 * | 4/2004 | Wong et al. ............ 424/422 |
| 6,841,684 B2 | 1/2005 | Chow et al. |
| 6,899,717 B2 | 5/2005 | Weber et al. |
| 7,033,605 B2 * | 4/2006 | Wong ..................... 424/427 |
| 7,048,946 B1 | 5/2006 | Wong et al. |
| 7,090,681 B2 | 8/2006 | Weber et al. |
| 7,091,232 B2 | 8/2006 | Chow et al. |
| 7,141,597 B2 | 11/2006 | Chow et al. |
| 7,147,644 B2 | 12/2006 | Weber et al. |
| 7,276,522 B2 | 10/2007 | Heidelbaugh et al. |
| 7,335,803 B2 | 2/2008 | Chow et al. |
| 7,468,065 B2 | 12/2008 | Weber et al. |
| 7,753,916 B2 | 7/2010 | Weber et al. |
| 7,767,223 B2 | 8/2010 | Wong |
| 8,034,366 B2 | 10/2011 | Nivaggioli et al. |
| 8,034,370 B2 | 10/2011 | Nivaggioli et al. |
| 8,043,628 B2 | 10/2011 | Wong |
| 8,048,445 B2 | 11/2011 | Nivaggioli et al. |
| 8,063,031 B2 * | 11/2011 | Wong et al. ............ 514/180 |
| 8,119,154 B2 | 2/2012 | Nivaggioli et al. |
| 2004/0019098 A1 | 1/2004 | Andrews et al. |
| 2004/0132824 A1 | 7/2004 | Gil et al. |
| 2004/0137059 A1 | 7/2004 | Nivagioli et al. |
| 2004/0151753 A1 | 8/2004 | Chen |
| 2004/0170665 A1 | 9/2004 | Donovan |
| 2004/0266776 A1 | 12/2004 | Gil et al. |
| 2005/0048099 A1 | 3/2005 | Shiah et al. |
| 2005/0058696 A1 | 3/2005 | Donello et al. |
| 2005/0059664 A1 | 3/2005 | Gil et al. |
| 2005/0059744 A1 | 3/2005 | Donello et al. |
| 2005/0101582 A1 | 5/2005 | Lyons et al. |
| 2005/0181017 A1 | 8/2005 | Hughes et al. |
| 2005/0232966 A1 | 10/2005 | Hughes et al. |
| 2005/0244464 A1 | 11/2005 | Hughes et al. |
| 2005/0244469 A1 | 11/2005 | Whitcup et al. |
| 2005/0244474 A1 | 11/2005 | Huang et al. |
| 2006/0009498 A1 | 1/2006 | Whitcup |
| 2006/0233857 A1 | 10/2006 | Amsden |
| 2006/0233859 A1 | 10/2006 | Whitcup et al. |
| 2007/0224246 A1 | 9/2007 | Hughes et al. |
| 2007/0298073 A1 | 12/2007 | Whitcup et al. |

FOREIGN PATENT DOCUMENTS

| | | |
|---|---|---|
| CA | 2336703 | 1/2000 |
| EP | 0 052 916 | 7/1981 |
| EP | 0 102 265 | 3/1984 |
| EP | 0 197 718 | 3/1986 |
| EP | 0 322 319 | 6/1989 |
| EP | 0 364 417 | 9/1989 |
| EP | 0430539 A2 | 11/1990 |
| EP | 0488401 | 11/1991 |
| EP | 0 474 098 | 3/1992 |
| EP | 0488 401 | 3/1992 |
| EP | 0654 256 | 2/1994 |
| EP | 0654256 | 2/1994 |
| EP | 0 311 065 | 10/1998 |
| EP | 0 992 244 | 4/2000 |
| WO | WO 91/15495 | 10/1991 |
| WO | WO 91/18940 | 12/1991 |
| WO | WO 92/21660 | 12/1992 |
| WO | WO 93/10141 | 5/1993 |
| WO | WO 94/03427 | 2/1994 |
| WO | WO 94/10202 | 5/1994 |
| WO | WO 94/14808 | 7/1994 |
| WO | WO 94/18956 | 9/1994 |
| WO | WO 95/13765 | 5/1995 |
| WO | WO 96/38174 | 12/1996 |
| WO | WO 97/26869 | 7/1997 |
| WO | WO 98/22130 | 5/1998 |
| WO | WO 99/11244 | 3/1999 |
| WO | WO 00/02564 | 1/2000 |
| WO | WO 00/37056 | 6/2000 |
| WO | WO 00/56340 | 9/2000 |
| WO | WO 00/62760 | 10/2000 |
| WO | WO 01/30323 | 5/2001 |
| WO | WO 02/02076 | 1/2002 |
| WO | WO 02/43785 | 6/2002 |
| WO | WO 03/094888 | 5/2003 |
| WO | WO 2004/026106 | 4/2004 |
| WO | WO 2004/062649 | 7/2004 |
| WO | WO 2005/110362 | 4/2005 |
| WO | WO 2006/093758 | 9/2006 |
| WO | WO 2007/130945 | 11/2007 |

OTHER PUBLICATIONS

Apel et al., A subconjunctival degradable implant for cyclosporine delivery in corneal transplant therapy; Current Eye Research; 1995; 659-667.

Aquilar, H.E. et al, (1995). "Vancomycin Levels After Intravitreal Injection", Retina 15: 428-432.

Araie, M. and Maurice, D.M. (1991). The Loss of Fluorescein, Fluorescein Glucoronide and Fluorescein Isothiocyanate Dextran From the Vitreous by the Anterior and Retinal Pathways >>, Exp. Eye. Res. 52, 27-39.

Barza, M. et al (1983). <<Pharmacokinetics of Intravitreal Carbenicillin, Cefazolin, and Gentamicin in Rhesus Monkey >>, Invest. Ophthalmol. Vis. Sci. 24: 1602-1606.

Ben-Nun, J. et al. (1989). "Pharmacokinetics of Intravitreal Injection", Investigative Ophthalmology & Visual Science 30(6): 1055-1061.

Bloch-Michel, Etienne; *Opening Address: Intermediate Uveitis*; Boke WRF, Manthey KF, Nussenblatt RB (eds): *Intermediate Uveitis*; Dev Ophthalmol; Basel, Karger; 1992, vol. 23; 1-2.

Bodor et al.; A comparison of intraocular pressure elevation activity of loteprednol etabonate and dexamethasone in rabbits: *Current Eye Research*, 1992, 11, 525-30.

Boke WRF, Manthey KF, Nussenblatt RB (eds). Clinical Picture of Intermediate Uveitis; *Intermediate Uveitis*: Dev Ophthalmol; Basel, Karger; 1992, vol. 23; 20-27.

Challa, J.K. et al (1998). <<Exudative Macular Degeneration and Intravitreal Triamcinolone : 18 month follow-up >>, Australian and New Zealand Journal of Ophthalmology 26 : 277-281.

Cheng et al.; Intravitreal Sustained-Release Dexamethasone Device in the Treatment of Experimental Uveitis; *Investigative Ophthalmology & Visual Science*; Feb. 1995, vol. 36, No. 2; 442-453.

De Jong et al.; New Insights into the hydrolytic degredation of poly (lactic acid): participation of the alcohol terminum; *Polymer* 42 (2001) 2795-2802.

Dohlman C. et al., *Treatment of corneal edema with a buried implant*, Tr. Am. Acad. Opth. & Otol., Mar.-Apr. 1966, pp. 267-280.

Enyedi, Laura et al., An Intravitreal Device Providing Sustained Release of Cyclosporine and Dexamethasone, Current Eye Research (1995) pp. 549-557.

Friedrich, S. et al (1997). "Finite Element Modeling of Drug Distribution in the Vitreous Humor of the Rabbit Eye", Annals of Biomedical Engineering 25: 303-314.

Gould et al.; Fifty:fifty poly (DL glycolic acid-lactic acid) copolymer as a drug delivery system for 5-fluorouracil: a histopathological evaluation; *Can J Ophthalmol*, vol. 29, No. 4, 1994; 168-171.

Hainsworth, Dean P. et al., Sustained Release Intravitreal Dexamethasone, Journal of Ocular Pharmacology and Therapeutics, (1996) vol. 12, No. 1, pp. 57-63.

Hayes, Robert C. Jr., Adrenocorticotropic Hormone: Adrenocortical Steroids and their Synthetic Analogs; Inhibitors of the Synthesis and Actions of Adrenocortical Hormones, Chapter 60 at p. 1447 of *Goodman and Gilman's: The pharmacological Basis of Therapeutics*, Eighth Edition, Pergamon Press1990.

Hayreh, S.S. (1996). "Posterior Drainage of the IntracularFluid From the Vitreous" Exp. Eye. Res. 5: 123-144.

Jaffe, G.J. et al (1999), "Safety, Efficacy, and Pharmacokinetics of an Intravitreal Fluocinolone Sustained Drug Delivered System", Investigative Ophthalmology & Visual Science 40 (4): 5988, Abstract No. 5195.

Jay, W.M. et al (1987). "Intravitreal Cefiazidine in a Rabbit Model: Dose-and Time-Dependent Toxicity and Pharmacokinetic Analysis,"J. Ocular Pharmcology 3 (3): 257-262.

Johnson, F. and Maurice D.(1984), "A Simple Method of Measuring Aqueous Humor Flow With Intravitreal Fluoresceinated Dextrans", Exp. Eye. Res. 39: 791-805.

Kane, A. et al (1981), "Intravitreal Injection of Gentamicin in Rabbits", Invest. Ophthalmol. Vis. Sci. 20(5): 593-597.

Kimura, H. and Ogura, Y (2001), "Biodegradable Polymers for Ocular Drug Delivery", Ophthalmologica 215: 143-155.

Kochinke, F. et al., Biodegradable Drug Delivery System for Uveitis Treatment. Investigative Ophthalmology & Visual Science. Feb. 15, 1996, vol. 37, No. 3, 186-B98.

Kralinger. M.T. et al (2001) "Slow Release of Acetylsalicyclic Acid by Intravitreal Silicone Oil", Retina, The Journal of Retinal and Vitreous Diseases, 21 (5): 513-530.

Kwak et al.; Evaluation of the Retinal Toxicity and Pharmacokinetics of Dexamethasone After Intravitreal Injection; *Arch Ophthalmol*, vol. 110, Feb. 1992, 259-266.

Laurent, U.B.G. and Fraser, J.R.E. (1983), "Turnover or Hyualuronate in the Aqueous Humor and Vitreous Body of the Rabbit", Exp. Eye. Res. 36: 493-504.

Lee et al.; Drug delivery to the posterior segment; Chapter 25 of *Principles of vitreoretinal therapy*, vol. 1, Part 1, 1989, 483-498.

Maurice, David M.; Micropharmaceutics of the Eye: *Ocular Inflammation Ther.*, 1; 1983, 97-102.

Maurice, D.M. and Mishima, S. (1984) Chapter 2: Ocular Pharmacokinetics, Handbook of Experimental Pharmacology, vol. 69, M.L. Sears (eds), Springer-Verlag, pp. 19-116.

Maurice, D.M. (1957), "The Exchange of Sodium Between the Vitreous Body and the Blood and Aqueous Humor", J. Physiol. 137: 110-125.

Maurice, D.M. (1987), "Flow of Water Between Aqueous and Vitreous Compartments in the Rabit Eye", Am. J. Physiol. 252 (Renal Fluid Electrolyte Physiol. 21): F104-F108.

Morita Y., et al., *Intravitreous delivery of dexamethasone sodium m-sulfobenzoate from poly(DL-lactic acid) implants*, Biol. Pharma. Bull., Feb. 1998; 21(2): 188-90.

Moseley H. et al (1984) "Routes of Clearance of Radioactive Water From the Rabbit Vitreous", British Journal of Ophthalmology 68: 145-151.

Nakamura O., et al., *Inhibition of neovascularization and tumor growth by dexamethasone*, No To Shinkei, Jan. 1992;44(1):37-41.

Ogden et al. editors; Retina—Basic Science and inherited Retinal Disease vol. 1, St. Louis; CV Mosby, (1989).

Ohtori, A. and Tojo, K. (1994) "In vivo/in vitro Correlation of Intravitreal Delivery of Drugs With the Help of Computer Simulation", Biol. Pharm. Bull. 17 (2): 283-290.

Olsen et al., Human Scleral Permeability—Effects of Age, Cryotherapy, Transscleral Diode Laser, and Surgical Thinning; *Investigative Ophthalmology & Visual Science*; Aug. 1995, vol. 36, No. 9, 1893-1903.

Park et al.; A new preparation method for protein loaded poly (D,L-lactic-coglycolic acid) Microspheres and protein release mechanism study; *Journal of Controlled Release*; 55 (1998), 181-191.

Pearson, P.A. et al (1993) "Clearance of Distribution of Ciprofloxacin After Intravitreal Injection", Retina 13: 326-330.

Renfro et al.; Ocular Effects of Topical and Systemic Steroids; *Dermatologic Clinics*, vol. 10, No. 3, Jul. 1992, 505-512.

Rootman, D.S. et al (1992), "Toxicity and Pharmacokinetics of Intravitreally Injection Ciprofloxacin in Rabbit Eyes", Can. J. Ophthalmol 27 (6): 277-282.

Sasaki, H. et al (1999), "Drug Absorption Behavior After Periocular Injections", Biol.Pharm. Bull. 22 (9): 956-960.

Schindler, R.H. et al (1982) "The Clearance of Intravitreal Triacinolone Acetonide", American Journal of Ophthalmology 93: 415-417.

Scholes, G.N. et al (1985) "Clearance of Tramcinolone From Vitreous", Arch. Ophthalmol. 103: 1567-1569.

Schwartz, Bernard; *The Response of Ocular Pressure to Corticosteroids*; Ophthalmol. Clin. North Am., 6: 929-89, (1966).

Skalka et al.; Effect of Corticosteroids on Cataract Formation; *Arch Ophthalmol*; vol. 98, Oct. 1980, 1773-1777.

Tracy et al., Factors affecting the degradation rate of poly (lactide-co-glycolide) Microspheres in vivo and in vitro; *Biomaterials*; 20 (1999), 1057-1062.

United States Pharmacopeia: The National Formulary 18; 1995, 1790-1798.

Xu, J. et al (2000) "Permeability and Diffusion in Vitreous Humor: Implications for Drug Delivery", Pharmaceutical Research 17 (6)664-667.

Zhou et al., "Development of a multiple-drug delivery implant for intraocular management of proliferative vitreoretinopathy"; *Journal of Controlled Release*; 55, 281-295, (1998).

Algvere, P.V., et al. "Transplantation of RPE in Age-Related Macular Degeneration: Observations in Disciform Lesions and Dry RPE Atrophy," *Graefe's Archives of Clinical Experimental Ophthalmology*, 1997; 235(3):149-158.

Anderson, L.C., et al. "An Injectable Substained Release Fertility Control System," *Contraception*, 1976; 13:375-384.

Andreau, K., et al. "Induction of apoptosis by dexamethasone in the B cell lineage," *Immunopharmacology*, Jul. 1998; 40(1):67-76.

Anteliff, R., et al. "The pathogenesis of edema in diabetic maculopathy," *Seminars in Ophthalmology*, 1999; 14:223-232.

Baker, R. "Monolithic Devices," *Controlled Release of Biologically Active Agents*, New York: John Wiley & Sons, 1987; 50-75.

Barnas, U., et al. "Parameters Associated with Chronic Renal Transplant Failure," *Nephrology Dialysis Transplantation*, 1997; 12(Suppl 2):82-85.

Beck, R.W., et al. "The Effect of Corticosteroids for Acute Optic Neuritis on the Subsequent Development of Multiple Sclerosis," *New England Journal of Medicine*, 1993; 329(24);1764-1769.

Beck, R.W., et al. "A randomized, controlled trial of corticosteroids in the treatment of acute optic neuritis," *New England Journal of Medicine*, Feb. 27, 1992; 326(9):634-5.

Bennett, W.M. and Barry, J.M. "Failure of Dexamethasone to Provide Adequate Chronic Immunosuppression for Renal Transplantation," *Transplantation*, 1979: 27(3):218-219.

Bigar, F. and C.P. Herbort. "Corneal Transplantation," *Current Opinion in Ophthalmology*, 1992; 3(4):473-481.

Bingaman, D.P., et al. "Inhibition of preretinal neovascularization in pigs by intravitreal triamcinolone acetonide," *Investigative Ophthalmology and Visual Science*, 1995; 36(4):S401, abstract 1867.

Bito, L.Z. "Prostaglandins and Related Compounds as Potential Ocular Therapeutic Agents," *Biological Protection with Prostaglandins*, vol. 1, Cohen, M.M. ed., Boca Raton: CRC Press Inc., 1985; 31-252.

Bito, L.Z. "Prostaglandins, Other Eicosanoids, and their Derivatives as Potential Antiglaucoma Agents," *Glaucoma: Applied Pharmacology in Medical Treatment*, Drance, S.M. and Neufled, A.H. Eds., New York: Grune & Stratton, 1984; 477-505.

Bito, L.Z. "Prostaglandins: Old Concepts and New Perspectives," *Archives of Ophthalmology*, 1987: 105:1036-1039.

Bolen, J.B. "Nonreceptor tyrosine protein kinases," *Oncogene*, 1993; 8(8):2025-2031.

Brubaker, R.F. "Mechanism of Action of Bimatoprost (Lumigan™)," *Survey of Ophthalmology*, 2001; 45(Suppl 4):S347-S351.

Budavari, S., et al. eds. *The Merck Index*, $12^{th}$ ed. Rahway, NJ: Merck and Co., 1996: Table of Contents only.

Bundgaard, H. and Møss, J. "Prodrugs of Peptides IV: Bioreversable Derivatization of the Pyroglutamyl Group by N-Acylation and N-Aminomethylation to Effect Protection against Pyroglutamyl Aminopeptidease," *Journal of Pharmaceutical Sciences*, 1989; 78(2):122-126.

Burdon, M.A. and P. McDonnell. "A Survey of Corneal Graft Practice in the United Kingdom," *Eye*, 1995; 9(Suppl):6-12.

Chacko, D.M., et al. "Survival and Differentiation of Cultured Retinal Progenitors Transplanted in the Subretinal Space of the Rat," *Biochemical and Biophysical Research Communications*, 2000; 268(3):842-846.

Chang, David, et al. "Phase II results of an intraocular steroid delivery system for cataract surgery," *Ophthalmology*, Jun. 1996; 106(6):1172-1177.

Chang, M., et al. "Basic Science and Clinical Aspects of Wound Healing in Glaucoma Filtering Surgery," *Journal of Ocular Pharmacology and Therapeutics*, 1998; 14(1):75-95.

Charles, J., et al. "Use of Bioerodible Polymers Impregnated with Mitomycin in Glaucoma Filtration Surgery in Rabbits," *Ophthalmology*, Apr. 1991; 98(4):503-508.

Chen, J., et al. "Lumigan®: A Novel Drug for Glaucoma Therapy," *Optometry in Practice*, 2002; 3:95-102.

Clarkson, J.G. "Central retinal vein occlusion," *Retina*, $3^{rd}$ ed. Ryan, S., Schachat, A.P., eds. St. Louis, MO: CV Mosby; 2001; 1368-1375.

Coleman, A.L., et al. "A 3-Month Randomized Controlled Trial of Bimatoprost (Lumigan) Versus Combined Timolol and Dorzolamide (Cosopt) in Patients with Glaucoma or Ocular Hypertension," *Ophthalmology*, 2003; 110(12):2362-2368.

Cuff, G. and Raouf, F. "A Preliminary Evaluation of Injection Molding as a Technology to Produce Tablets," *Pharmaceutical Technology*, 1998; 96-106.

Davis, P.A., et al. "Intraocular Implant for Controlled 5-Fluorouracil Release," *Proceedings of the 19th International Symposium of Controlled Release Bioactive Materials*, 1992; 19:339-340.

Di Colo, G. "Controlled Drug Release From Implantable Matrices Based on Hydrophobic Polymers," *Biomaterials*, 1992; 13(12):850-856.

Dick, J., et al. "Macular edema," *Retina*, $3^{rd}$ ed. Ryan, S., Schachat, A.P., eds. St. Louis, MO: CV Mosby; 2001; 967-979.

Dinning, W.J. "Intermediate Uveitis: history, terminology definition pars planitis: systemic disease associations," *Developments in Ophthalmology: Intermediate Uveitis*, W.R.F. Böke, et al. eds, Basel: Karger, 1992; 3-8.

Druilhe, A., et al. "Glucocorticoid-induced apoptosis in human eosinophils: mechanisms of action," *Apoptosis*, Oct. 2003; 8(5);481-95.

*Encyclopedia of Polymer Science and Technology*, vol. 3. New York: Interscience Publishers, Inc., 2003; Table of Contents only, v.

Enzmann, V., et al. "Immunological Problems of Transplantation into the Subretinal Space," *Acta Anatomica*, 1998; 162(2-3):178-183.

Fatt, I. "Flow and Diffusion in the Vitreous Body of the Eye," *Bulletin of Mathematical Biology*, 1975; 37:85-90.

Fekrat, S. and Finkelstein, D. "The Central Vein Occlusion Study," *Clinical trials in ophthalmology: a summary and practice guide*, Kertes, P.S., Conway, M.D., eds. Baltimore, MD: Williams & Wilkins, 1998; 129-143.

Frank, R.N. "Etiologic mechanisms in diabetic retinopathy," *Retina*, $3^{rd}$ ed. Ryan, S., Schachat,, A.P., eds. St. Louis, MO: CV Mosby; 2001; 1259-1294.

Gennaro, A.R. ed. *Remington: The Science and Practice of Pharmacy*, $19^{th}$ Ed. Easton, PA: Mack Publishing Company, 1995; Table of Contents only, xv-xvi.

Gillies, M.C., et al. "Safety of an intravitreal injection of triamcinolone," *Archives of Ophthalmology*, Mar. 2004; 122:336-340.

Gilman, A.G., et al. eds. *Goodman and Gilman's: The Pharmacological Basis of Therapeutics*. $8^{th}$ Ed. New York: Pergamon Press, 1990; Table of Contents only, xi-xvi.

Goldberg, Ivan, "Drugs for glaucoma," *Australian Prescriber*, 2002; 25(6)142-146.

Goodman, L.S. and A. Gilman eds. *The Pharmacological Basis of Therapeutics*, $9^{th}$ Ed. New York: McGraw-Hill, 1996; Table of Contents only, v-xii.

Greenfield, R.S., et al. "Evaluation in vitro of Adriamycin Immunoconjugates Synthesized Using an Acid-sensitive Hydrazone Linker," *Cancer Research*, 1990; 50:6600-6607.

Guan, D., et al. "The Therapeutic Window of Cyclosporine in Chinese Recipients of Renal Transplantation," *Transplantation Proceedings*, 1995; 27(1) 850-851.

Hari, P. and Srivastava, R.N. "Pulse Corticosteroid Therapy with Methylprednisolone or Dexamethasone," *Indian Journal of Pediatrics*, 1998; 65(3):557-560.

Heller, J. "Biodegradable Polymers in a Controlled Drug Delivery," *CRC Critical Reviews in Therapeutic Drug Carrier Systems*, 1984; 1(1):39-90.

Heller, J. "Bioerodible Hydrogels," *Hydrogels in Medicine and Pharmacy, vol. 3: Properties and Applications*, Peppas, N.A. ed. Boca Raton: CRC Press, 1987; 138-149.

Heller, J. "Poly (Ortho Esters)," *Biopolymers I*, Peppas, N.A. and R.S. Langer eds. New York: Springer-Verlag, 1993; 41-92.

Heller, J., et al. "Poly(ortho ester) Biodegradable Polymer Systems," *Methods in Enzymology*, Widder, K.J. and R. Green eds. Orlando: Academic Press, Inc , 1985; 422-436.

Hirano, T. "Clinical Significance of Glucocorticoid Pharmacodynamics Assessed by Antilymphocyte Action in Kidney Transplantation," *Transplantation*, 1994; 57(9):1341-1348.

Höckel, M., et al. "Prevention of Peritoneal Adhesions in the Rat With Sustained Intraperitoneal Dexamethasone Delivered by a Novel Therapeutic System," *Annales Chirurgiae et Gynaecologiae*, 1987; 76(6):306-313.

Inoue, M., et al. "Vitreous Concentrations of Triamcinolone Acetonide in Human Eyes After Intravitreal or Subtenon Injection," *American Journal of Ophthalmology*, 2004; 138(6):1046-8.

Jackanicz, T., et al. "Polyactic Acid as a Biogradable Carrier for Contraceptive Steroids" *Contraception*, 1973; 8(3):227-234.

Jaffe, G.J., et al. "Safety and Pharmacokinetics of an Intraocular Fluocinolone Acetonide Sustained Delivery Device," *Investigative Ophthalmology & Visual Science*, 2000; 41(11):3569-3575.

Jampel, H., et al. "Glaucoma Filtration Surgery in Monkeys Using 5-Fluorouridine in Polyanhydride Disks," *Archives of Ophthalmology*, Mar. 1990; 108(3):430-435.

Jellinek, D., et al. "Inhibition of Receptor binding by High-affinity RNA Ligands to Vascular Endothelial Growth Factor," *Biochemistry*, 1994; 33:10450-56

Jennings, T., et al. "Posterior sub-Tenon's injections of corticosteroids in uveitis patients with cystoid macular edema," *Japanese Journal of Ophthalmology*, 1988; 32(4):385-391.

Jeong, J.H., et al. "Novel Intracellular Delivery System of Antisense Oligonucleotide by Self-Assembled Hybrid Micelles Composed of DNA/PEG Conjugate and Cationic Fusogenic Peptide," *Bioconjugate Chemistry*, 2003; 14:473-479.

Jonas, J.B., et al. "Intraocular pressure after intravitreal injection of triamcinolone acetonide," *British Journal of Ophthalmology*, 2003; 87:24-27.

Kang, S,W., et al. "Macular grid photocoagulation after intravitreal triamcinolone acetonide for diffuse diabetic macular edema," *Archives of Ophthalmology*, May 2006; 124(5):653-8.

Kendall, R.L. and K.A. Thomas. "Inhibition of vascular endothelial cell growth factor activity by an endogenously encoded soluble receptor," *Proceedings of the National Academy of Science USA*, 1994; 90:10705-09.

Kher, V., et al. "Low-Dose Dexamethasone—An Alternative Therapy for Acute Renal Allograft Rejection," *Transplantation Proceedings*, 1992; 24(5):1725.

Kim, K.J., et al. "Inhibition of vascular endothelial growth factor-induced angiogenesis suppresses tumour growth in vivo," *Nature*, 1993; 362(6423):841-844.

Kinsella, J.L., et al. "Protein Kinase C Regulates Endothelial Cell Tube Formation on Basement Membrane Matrix, Matrigel," *Experimental Cell Research*, 1992; 199:56-62.

Kunou, Noriyuki, et al. "Biodegradable scleral implant for controlled intraocular delivery of betamethasone phosphate," *Journal of Biomedical Materials Research*, 2000; 51(4):635-641.

Lee, D., et al, "Complications of Subconjunctival 5-Fluorouracil Following Glaucoma Filtering Surgery," *Ophthalmic Surgery*, Mar. 1987; 18(3):187-190.

Lee, D., et al. "Glaucoma Filtration Surgery in Rabbits Using Bioerodible Polymers and 5-Fluorouracil," *Ophthalmology*, Dec. 1987; 94(12):1523-1530.

Lee, D., et al. "The Use of Bioerodible Polymers and 5-Fluorouracil in Glaucoma Filtration Surgery," *Investigative Ophthalmology & Visual Science*, Nov. 1988; 29(11):1692-1697.

Lee, K.Y. and Wong, V.G. "Dexamethasone Posterior Segment Drug Delivery System for Treatment of Severe Uveitis," *American Uveitis Society*, 1999; Abstract.

Leopold, I.H. "Nonsteroidal and steroidal anti-inflammatory agents," *Surgical pharmacology of the Eye*, Sears, M., Tarkkanen, A., eds. New York: Raven Press, 1985; 83-133.

Marcon, I. "A double-masked comparison of betaxolol and levobunolol for the treatment of primary open-angle glaucoma," *Arquivos Brasileiros de Oftalmologia*, 1990; 53(1):27-32.

Mariani, M., et al. "Inhibition of FCE 26806, a potent tyrosine kinase inhibitor," *Proceedings of the American Association for Cancer Research*, 1994; 35:381, abstract 2268.

Mathebula, S.D. "A Review of Pharmacological Therapy for Glaucoma," *The South African Optometrist*, Sep. 2005; 64(3):89-96.

Meadows, D.L., et al. "Ocular Drug Delivery with Subconjunctival Implants," *Proceedings of the International Symposium on Controlled Release of Bioactive Materials*, Controlled Release Society, Inc., 1994; 21:593-594.

Migita, K., et al. "Apoptosis Induction in Human Peripheral Blood T Lymphocytes by High-Dose Steroid Therapy", *Transplantation*, 1997; 63(4):583-587.

Miller, R., et al. "Degradation Rates of Oral Resorbable Implants (Polylactates and Polyglycolates): Rate Modification with Changes in PLA/PGA Copolymer Ratios," *Journal of Biomedical Materials Research*, 1977; 11(5):711-719.

Mittal, R., et al. "Treatment of Acute Rejection in Live Related Renal Allograft Recipients: A Comparison of Three Different Protocols," *Nephron*, 1977; 77(2):186-189.

Molfino, F., et al. "IOP-lowering effect of dorzolamide 2% versus brimonidine tartrate 0.2%. A prospective randomized cross over study," *Investigative Ophthalmology & Visual Science*, Mar. 1998; 39(4):S481.

Morita, Y., et al. "Polymer Blend Implant for Ocular Delivery of Fluorometholone," *Biological & Pharmaceutical Bulletin*, 1998; 21(1):72-75.

Nauck, M., et al. "Corticosteroids inhibit the expression of the vascular endothelial growth factor gene in human vascular smooth muscle cells," *European Journal of Pharmacology*, 1998; 341:309-315.

Nauck, M., et al. "Induction of vascular endothelial growth factor by platelet-activating factor and platelet-derived growth factor is downregulated by corticosteroids," *American Journal of Respiratory Cell and Molecular Biology*, 1997; 16:398-406.

Nilsson, S.F.E., et al. "PGF2 Increases Uveoscleral Outflow," *Investigative Ophthalmology & Visual Science*, 1987; 28(3):284, abstract 9.

Oplinger, N.L., et al. "A Comparison of Corneal Autografts With Homografts," *Ophthalmic Surgery and Lasers*, 1998; 29(4):305-308.

Orth, D. "The branch vein occlusion study," *Clinical trials in ophthalmology: A summary and practice guide*, Kertes, P, and Conway, M, eds., Baltimore, MD: Williams & Wilkins, 1998: 113-127.

Patel, N.P., et al. "Indications for and Outcomes of Repeat Penetrating Keratoplasty, 1989-1995," *Ophthalmology*, 2000; 107(4):719-724.

Peter, J., et al. "Vascular endothelial growth factor by platelet-activating factor upregulation in human central retinal vein occlusion," *Ophthalmology*, 1998; 105:412-416.

Peyman, G.A. and Herbst, R. "Bacterial endophthalmitis," *Archives of Ophthalmology*, 1974; 91(5):416-418.

Peyman, G.A., et al. "A Technique for Retinal Pigment Epithelium Transplantation for Age-Related Macular Degeneration Secondary to Extensive Subfoveal Scarring," *Ophthalmic Surgery*, 1991; 22(2):102-108.

Pinar, V. "Intermediate Uveitis," *Massachusetts Eye & Ear Infirmary Immunology Service*, Boston.

Plowman, G.D., et al. "Receptor Tyrosine Kinases as Targets for Drug Intervention," *Drug News & Perspectives*, 1994; 7(6):334-339.

Rahil, J., et al. "Reactivity and Mechanism of Hydrolysis of Phosphonamides," *Journal of the American Chemical Society*, 1981; 103:1723-1734.

Rao, K.V., et al. "Successful Renal Transplantation in a Patient With Anaphylactic Reaction to Solu-Medrol (Methylprednisolone Sodium Succinate)," *American Journal of Medicine*, 1982; 72(1):161-163.

Riordan-Eva, P., et al. "Orbital floor steroid injections in the treatment of uveitis," *Eye*, 1994; 8(1):66-69.

Robin, Jeffrey B., et al. "The Histopathology of Corneal Neovascularization," *Archives of Ophthalmology*, 1985; 103(2):284-287.

Roff, W.J. and Scott, J.R. eds. *Handbook of Common Polymers*, Cleveland: CRC Press, 1971; Table of Contents.

Schimmer B.P. and Parker K.L. "Adrenocorticotrophic hormone, Adrenocortical Steroids and their Synthetic Analogs; Inhibitors of the Synthesis and Actions of Adrenocortical Hormones," *The Pharmacological Basis of Therapeutics $10^{th}$ ed.*, Hardman, J.G. and Limbard, L.L. eds, New York: McGraw-Hill, 2001; 1649-1677.

Scholes, G.N., et al. "Clearance of Triamcinolone From Vitreous," *Archives of Ophthalmology*, 1985; 103(10):1567-1569.

Scott, J.R. and W.J. Roff eds. "Permeability," *Handbook of Common Polymers*, Cleveland: CRC Press, 1971; 554-558.

Shields, Bruce M. "Glaucoma Filtering Procedures," *A Study Guide for Glaucoma*, Baltimore: Williams & Wilkins, 1982; 453-476.

Siebold, et al. *Prodrug*, 1989; 5:3.

Smith, T., et al. "Sustained-release subconjunctival 5-Fluorouracil," *Ophthalmic Surgery and Lasers*, Sep. 1996; 27(9):763-767.

Starr, M.S. "Further Studies on the Effect of Prostaglandin on Intraocular Pressure in the Rabbit," *Experimental Eye Research*, 1971; 11(2):170-177.

Stewart, W., et al. "Washout periods for brimonidine 0.2% and latanoprost 0.005%," *American Journal of Ophthalmology*, Jun. 2001; 131(6):798-799.

Taba, K.E., et al. "Intravitreal sustained release fluocinolone implant inhibits experimental choroidal neovascularization," *Investigative Ophthalmology & Visual Science*, Mar. 1999; 40(4):S172, abstract 920.

Takano, S.,et al. "Inhibition of Angiogenesis by a Novel Diaminoanthraquinone that Inhibits Protein Kinase C," *Molecular Biology of the Cell*, 1993; 4:358A, abstract 2076.

Tan, D.T.H., et al. "Randomized Clinical Trial of a New Dexamethasone Delivery System (Surodex) for Treating of Post-Cataract Surgery Inflammation," *Ophthalmology*, 1999; 106(2):223-231.

Tennant, J.L. "Cystoid maculopathy," *Current concepts in cataract surgery: selected proceedings of the fifth biennial cataract surgical congress*, Emery, J.M. ed. St. Louis: CV Mosby, 1978:360-362.

Theng, J.T.S., et al. "Pharmacokinetic and Toxicity Study of an Intraocular Cyclosporine DDS in the Anterior Segment of Rabbit Eyes," *Investigative Ophthalmology & Visual Science*, Nov. 2003; 44(11):4895-4899.

Tsubota, K. "Ocular Surface Managment in Corneal Transplantation, A Review," *Japanese Journal of Ophthalmology*, 1999; 43(6):502-508.

Turcotte, J.G., et al. "Rejection Crises in Human Renal Transplant Recipients: Control with High Dose Methylprednisolone Therapy," *Archives of Surgery*, 1972; 105(1):230-236.

*The United States Pharmacopeia, The National Formulary*, "USP 24/NF 19," 2000; 1941-1951.

Watson, P., et al. "A Six-month, Randomized, Double-masked Study Comparing Latanoprost with Timolol in Open-angle Glaucoma and Ocular Hypertension," *Ophthalmology*, 1996; 103(1):126-137.

Weisbecker, C.A., et al., eds. *Physicians' Desk Reference for Ophthalmology 27th ed.*, Montvale, NJ: Medical Economics Company, 1998; 7-8, 278-279.

Wingate, R.J., et al. "Intravitreal Triamcinolone and Elevated Intraocular Pressure," *Australian and New Zealand Journal of Ophthalmology*, Dec. 1999; 27(6):431-2.

Woodward, D.F., et al. "AGN 192024 (Lumigan®): A Synthetic Prostamide Analog that Lowers Primate Intraocular Pressure by Virtue of its Inherent Pharmacological Activity," *Investigative Ophthalmology & Visual Science*, 2002; 43, abstract 4110.

Woodward, D.F., et al. "The Pharmacology of Bimatoprost (Lumigan™)," *Survey of Ophthalmology*, 2001; 45(Suppl 4):S337-S345.

Wright, P.S., et al. "Inhibition of Angiogenesis In Vitro and In Ovo with an Inhibitor of Cellular Protein Kinases, MDL 27032," *Journal of Cellular Physiology*, 1992; 152(3):448-457.

Vakur Pinar. MD, "Intermediate Uveitis", Case Presentation, Immunology and Uveitis Service, Massachusetts Eye and Ear Infirmary, 8 pages, Feb. 3, 2005, www.uveitis.org/medical/articles/case/imede.html.

* cited by examiner

IMPLANTS AND METHODS FOR TREATING INFLAMMATION-MEDIATED CONDITIONS OF THE EYE

CROSS-REFERENCE TO OTHER APPLICATIONS

This application is a continuation of U.S. patent application Ser. No. 12/646,522, filed Dec. 23, 2009, now U.S. Pat. No. 8,063,031 and hereby incorporated by reference, which is a continuation of U.S. patent application Ser. No. 10/671,816, filed Sep. 25, 2003, now abandoned, which is a continuation of U.S. patent application Ser. No. 09/693,008, filed Oct. 20, 2000, hereby incorporated by reference, and now U.S. Pat. No. 6,726,918, which claims priority to U.S. Provisional Application Ser. No. 60/216,236, filed Jul. 5, 2000, and hereby incorporated by reference.

TECHNICAL FIELD

This invention relates to methods for treating inflammation-mediated conditions of the eye by implanting into the vitreous of the eye a bioerodible implant comprising a steroidal anti-inflammatory agent and a bioerodible polymer. Specifically, these methods may be used in the protection and treatment of tissues damaged by or susceptible to damage by inflammation-mediated conditions such as uveitis, by providing therapeutic levels of an anti-inflammatory agent to the vitreous of the eye.

BACKGROUND ART

Glucocorticoids are an important part of treatment in severe anterior, intermediate, posterior, and panuveitis. A major problem with present drug therapy is the inability to achieve adequate intraocular drug concentration. In particular, uveitis is well known for its long duration due in part to the difficulties associated with poor intraocular penetration of topical medications into the posterior segment (Bloch-Michel E. (1992). "Opening address: intermediate uveitis," In *Intermediate Uveitis, Dev Ophthalmol*. W. R. F. Böke et al. eds., Basel: Karger, 23:1-2; Pinar, V. Intermediate uveitis. Massachusetts Eye & Ear Infirmary Immunology Service at www.immunology.meei.harvard.edulimed.htm (visited in 1998); Rao, N. A. et al. (1997). "Intraocular inflammation and uveitis" In *Basic and Clinical Science Course*. Section 9 (1997-1998) San Francisco: American Academy of Ophthalmology, pp. 57-80, 102-103, 152-156; Böke, W. (1992). "Clinical picture of intermediate uveitis," In *Intermediate Uveitis, Dev Ophthalmol*. W. R. F. Böke et al. eds., Basel: Karger, 23:20-7; Cheng C-K et al. (1995). "Intravitreal sustained-release dexamethasone device in the treatment of experimental uveitis," *Invest Ophthalmol Vis Sci*. 36:442-53). Systemic glucocorticoid administration may require prolonged exposure of high plasma concentrations (administration of 1 mg/kg/day for 2-3 weeks) so that therapeutic levels can be achieved in the eye (Pinar, V. "Intermediate uveitis," Massachusetts Eye & Ear Infirmary Immunology Service at www.immunology.meei.harvard.edulimed.htm (visited in 1998)). These high drug plasma levels often lead to systemic side effects such as hypertension, hyperglycemia, increased susceptibility to infection, peptic ulcers, psychosis, and other complications (Cheng C-K et al. (1995). "Intravitreal sustained-release dexamethasone device in the treatment of experimental uveitis," *Invest Ophthalmol Vis Sci*. 36:442-53; Schwartz, B. (1966). "The response of ocular pressure to corticosteroids," *Ophthalmol Clin North Am* 6:929-89; Skalka, H. W. et al. (1980). "Effect of corticosteroids on cataract formation," *Arch Ophthalmol* 98:1773-7; Renfro, L. et al. (1992). "Ocular effects of topical and systemic steroids," *Dermatologic Clinics* 10:505-12). In addition, overall drug delivery to the eye may be poor due to the short drug plasma half-life limiting exposure into intraocular tissues. The most efficient way of delivering drug to the posterior segment is to place it directly in the vitreous (Maurice, D. M. (1983). "Micropharmaceutics of the eye," *Ocular Inflammation Ther* 1:97-102; Lee, V. H. L. et al. (1989). "Drug delivery to the posterior segment" Chapter 25 In *Retina*. T. E. Ogden and A. P. Schachat eds., St. Louis: CV Mosby, Vol. 1, pp. 483-98; Olsen, T. W. et al. (1995). "Human scleral permeability: effects of age, cryotherapy, transscleral diode laser, and surgical thinning," *Invest Ophthalmol Vis Sci* 36:1893-1903). Intravitreal injections have shown promising results, however, due to the short intraocular half-life of glucocorticoids (approximately 3 hours), intravitreal injections must be repeated to maintain drug levels which increases the potential for side effects such as retinal detachment, endophthalmitis, and cataract (Maurice, D. M. (1983). "Micropharmaceutics of the eye," *Ocular Inflammation Ther* 1:97-102; Olsen, T. W. et al. (1995). "Human scleral permeability: effects of age, cryotherapy, transscleral diode laser, and surgical thinning," *Invest Ophthalmol Vis Sci* 36:1893-1903; Kwak, H. W. and D'Amico, D. J. (1992). "Evaluation of the retinal toxicity and pharmacokinetics of dexamethasone after intravitreal injection," *Arch Ophthalmol* 110:259-66). Topical, systemic, and periocular glucocorticoid treatment must be monitored closely due to toxicity and the long-term side effects associated with chronic systemic drug exposure sequelae (Rao, N. A. et al. (1997). "Intraocular inflammation and uveitis" In *Basic and Clinical Science Course*. Section 9 (1997-1998) San Francisco: American Academy of Ophthalmology, pp. 57-80, 102-103, 152-156; Schwartz, B. (1966). "The response of ocular pressure to corticosteroids," *Ophthalmol Clin North Am* 6:929-89; Skalka, H. W. and Pichal, J. T. (1980). "Effect of corticosteroids on cataract formation," *Arch Ophthalmol* 98:1773-7; Renfro, L and Snow, J. S. (1992). "Ocular effects of topical and systemic steroids," *Dermatologic Clinics* 10:505-12; Bodor, N. et al. (1992). "A comparison of intraocular pressure elevating activity of loteprednol etabonate and dexamethasone in rabbits," *Current Eye Research* 11:525-30).

U.S. Pat. No. 5,501,856 discloses controlled-release pharmaceutical preparations for intraocular implants to be applied to the interior of the eye after a surgical operation for disorders in retina/vitreous body or for glaucoma.

U.S. Pat. No. 5,869,079 discloses combinations of hydrophilic and hydrophobic entities in a biodegradable sustained release implant, and describes a polylactic acid polyglycolic acid (PLGA) copolymer implant comprising dexamethasone. As shown by in vitro testing of the drug release kinetics, the 100-120 µg 50/50 PLGA/dexamethasone implant disclosed did not show appreciable drug release until the beginning of the fourth week.

U.S. Pat. No. 5,824,072 discloses implants for introduction into a suprachoroidal space or an avascular region of the eye, and describes a methylcellulose implant comprising dexamethasone.

U.S. Pat. Nos. 4,997,652 and 5,164,188 disclose biodegradable ocular implants comprising microencapsulated drugs, and describes implanting microcapsules comprising hydrocortisone succinate into the posterior segment of the eye.

U.S. Pat. No. 5,164,188 discloses encapsulated agents for introduction into the suprachoroid of the eye, and describes placing microcapsules and plaques comprising hydrocortisone into the pars plana.

U.S. Pat. Nos. 5,443,505 and 5,766,242 discloses implants comprising active agents for introduction into a suprachoroidal space or an avascular region of the eye, and describes placing microcapsules and plaques comprising hydrocortisone into the pars plana.

Zhou et al. disclose a multiple-drug implant comprising 5-fluorouridine, triamcinolone, and human recombinant tissue plasminogen activator for intraocular management of proliferative vitreoretinopathy (PVR) (Zhou, T, et al. (1998). "Development of a multiple-drug delivery implant for intraocular management of proliferative vitreoretinopathy," *Journal of Controlled Release* 55: 281-295.)

There is a continued need for efficacious intraocular sustained release drug therapies for patients with inflammatory conditions.

All references cited herein are hereby incorporated by reference in their entirety.

DISCLOSURE OF THE INVENTION

The present invention provides a method for treating an inflammation-mediated condition of the eye, comprising: implanting into the vitreous of the eye a bioerodible implant comprising a steroidal anti-inflammatory agent and a bioerodible polymer, wherein the implant delivers the agent to the vitreous in an amount sufficient to reach a concentration equivalent to at least about 0.05 µg/ml dexamethasone within about 48 hours and maintains a concentration equivalent to at least about 0.03 µg/ml dexamethasone for at least about three weeks.

In another embodiment of the invention, a method for treating an inflammation-mediated condition of the eye is provided, comprising: implanting a solid body into the vitreous of the eye, said body comprising particles of a steroidal anti-inflammatory agent entrapped within a bioerodible polymer, whereby said agent is released from the body by erosion of the polymer, and whereby said agent is delivered to the vitreous at a rate and for a time sufficient to reach a concentration equivalent to at least about 0.05 µg/ml dexamethasone within about 48 hours, and maintains a concentration equivalent to at least about 0.03 µg/ml dexamethasone for at least about three weeks.

In another embodiment of the invention, a method for treating an inflammation-mediated condition of the eye is provided, comprising: implanting into the vitreous of the eye a bioerodible implant comprising a steroidal anti-inflammatory agent and a bioerodible polymer, wherein the implant delivers the agent to the vitreous in an amount sufficient to reach a concentration equivalent to at least about 0.2 µg/ml dexamethasone within about 6 hours and maintains a concentration equivalent to at least about 0.01 µg/ml dexamethasone for at least about three weeks.

In another embodiment of the invention, a method for treating an inflammation-mediated condition of the eye is provided, comprising: implanting a solid body into the vitreous of the eye, said body comprising particles of a steroidal anti-inflammatory agent entrapped within a bioerodible polymer, whereby said agent is released from the body by erosion of the polymer, and whereby said agent is delivered to the vitreous at a rate and for a time sufficient to reach a concentration equivalent to at least about 0.2 µg/ml dexamethasone within about 6 hours, and maintains a concentration equivalent to at least about 0.01 µg/ml dexamethasone for at least about three weeks.

MODES FOR CARRYING OUT THE INVENTION

Definitions

As used herein, the term "inflammation-mediated condition of the eye" is meant to include any condition of the eye which may benefit from treatment with an anti-inflammatory agent, and is meant to include, but is not limited to, uveitis, macular edema, acute macular degeneration, retinal detachment, ocular tumors, fungal or viral infections, multifocal choroiditis, diabetic uveitis, proliferative vitreoretinopathy (PVR), sympathetic ophthalmia, Vogt Koyanagi-Harada (VKH) syndrome, histoplasmosis, and uveal diffusion.

The term "bioerodible polymer" refers to polymers which degrade in vivo, and wherein erosion of the polymer over time is required to achieve the agent release kinetics according to the invention. Specifically, hydrogels such as methylcellulose which act to release drug through polymer swelling are specifically excluded from the term "bioerodible polymer". The terms "bioerodible" and "biodegradable" are equivalent and are used interchangeably herein.

The terms "steroidal anti-inflammatory agent" and "glucocorticoid" are used interchangeably herein, and are meant to include steroidal agents, compounds or drugs which reduce inflammation when administered at a therapeutically effective level.

"A concentration equivalent to dexamethasone", as used herein, refers to the concentration of a steroidal anti-inflammatory agent necessary to have approximately the same efficacy in vivo as a particular dose of dexamethasone. For example, hydrocortisone is approximately twentyfivefold less potent than dexamethasone, and thus a 25 mg dose of hydrocortisone would be equivalent to a 1 mg dose of dexamethasone. One of ordinary skill in the art would be able to determine the concentration equivalent to dexamethasone for a particular steroidal anti-inflammatory agent from one of several standard tests known in the art. Relative potencies of selected corticosteroids may be found, for example, in Gilman, A. G., et al., eds. (1990). *Goodman and Gilman's: The Pharmacological Basis of Therapeutics.* 8th Edition, Pergamon Press: New York, p. 1447.

An "individual" is a vertebrate, preferably mammal, more preferably a human. Mammals include, but are not limited to, humans, sport animals and pets, such as dogs, horses.

The terms "injury" or "damage" as used herein are interchangeable and refer to the cellular and morphological manifestations and symptoms resulting from an inflammatory-mediated condition, such as, for example, inflammation.

The term "treating" as used herein, means to reduce or prevent ocular injury or damage.

The term "therapeutic levels" as used herein, refers to the level of agent needed to reduce or prevent ocular injury or damage.

By "measured under infinite sink conditions in vitro," is meant assays to measure drug release in vitro, wherein the experiment is designed such that the drug concentration in the receptor medium never exceeds 5% of saturation. Examples of suitable assays may be found, for example, in (USP 23; NF 18 (1995) pp. 1790-1798).

"A", "an" and "the" include plural references unless the context clearly dictates otherwise.

Methods for Treating an Inflammation-Mediated Condition

Intraocular glucocorticoid drug delivery systems made of a biodegradable polymer matrix have been developed which can release drug loads over various programmed time periods. These drug delivery systems which when inserted into the vitreous provide therapeutic levels of glucocorticoid for extended periods of time (e.g., 3 weeks or more). In particular, these delivery systems provide an initial "loading dose" level of drug of at least about 0.05 µg/ml dexamethasone equivalent to the posterior segment of the eye. These delivery systems have shown unexpected results in treating diseases such as uveitis and PVR.

Accordingly, the present invention provides a method for treating an inflammation-mediated condition of the eye, comprising: implanting into the vitreous of the eye a bioerodible implant comprising a steroidal anti-inflammatory agent and a bioerodible polymer, wherein the implant delivers the agent to the vitreous in an amount sufficient to reach a concentration equivalent to at least about 0.05 µg/ml dexamethasone within about 48 hours and maintains a concentration equivalent to at least about 0.03 µg/ml dexamethasone for at least about three weeks.

In another embodiment of the invention, a method for treating an inflammation-mediated condition of the eye is provided, comprising: implanting a solid body into the vitreous of the eye, said body comprising particles of a steroidal anti-inflammatory agent entrapped within a bioerodible polymer, whereby said agent is released from the body by erosion of the polymer, and whereby said agent is delivered to the vitreous at a rate and for a time sufficient to reach a concentration equivalent to at least about 0.05 µg/ml dexamethasone within about 48 hours, and maintains a concentration equivalent to at least about 0.03 µg/ml dexamethasone for at least about three weeks.

In another embodiment of the invention, a method for treating an inflammation-mediated condition of the eye is provided, comprising: implanting into the vitreous of the eye a bioerodible implant comprising a steroidal anti-inflammatory agent and a bioerodible polymer, wherein the implant delivers the agent to the vitreous in an amount sufficient to reach a concentration equivalent to at least about 0.2 µg/ml dexamethasone within about 6 hours and maintains a concentration equivalent to at least about 0.01 µg/ml dexamethasone for at least about three weeks.

In another embodiment of the invention, a method for treating an inflammation-mediated condition of the eye is provided, comprising: implanting a solid body into the vitreous of the eye, said body comprising particles of a steroidal anti-inflammatory agent entrapped within a bioerodible polymer, whereby said agent is released from the body by erosion of the polymer, and whereby said agent is delivered to the vitreous at a rate and for a time sufficient to reach a concentration equivalent to at least about 0.2 µg/ml dexamethasone within about 6 hours, and maintains a concentration equivalent to at least about 0.01 µg/ml dexamethasone for at least about three weeks.

Preferred inflammation-mediated conditions of the eye which may be treated by the methods of the invention include uveitis, macular edema, acute macular degeneration, retinal detachment, ocular tumors, fungal or viral infections, multifocal choroiditis, diabetic uveitis, proliferative vitreoretinopathy (PVR), sympathetic ophthalmia, Vogt Koyanagi-Harada (VKH) syndrome, histoplasmosis, and uveal diffusion. In a preferred embodiment, the inflammation-mediated condition of the eye is uveitis. In another preferred embodiment, the inflammation-mediated condition of the eye is proliferative vitreoretinopathy (PVR).

The delivery systems are designed to release the glucocorticoid at therapeutic levels to the vitreous for a sustained period of time. In one embodiment, the implant delivers the agent to the vitreous in an amount sufficient to reach a concentration equivalent to at least about 0.05 µg/ml dexamethasone within about 48 hours. In other embodiments, the implant delivers the agent to the vitreous in an amount sufficient to reach a concentration equivalent to at least about 0.06 µg/ml, at least about 0.07 µg/ml, at least about 0.08 µg/ml, at least about 0.1 µg/ml, at least about 0.125 µg/ml, at least about 0.15 µg/ml dexamethasone within about 48 hours.

In another embodiment, the implant delivers the agent to the vitreous in an amount sufficient to reach a concentration equivalent to at least about 0.2 µg/ml dexamethasone within about 6 hours. In other embodiments, the implant delivers the agent to the vitreous in an amount sufficient to reach a concentration equivalent to at least about 0.3 µg/ml, at least about 0.5 µg/ml, at least about 0.75 µg/ml, at least about 1.0 µg/ml, at least about 2.0 µg/ml dexamethasone within about 4 hours, within about 6 hours, within about 8 hours, within about 10 hours, within about 24 hours.

A concentration equivalent to at least about 0.01 µg/ml, at least about 0.02 µg/ml, at least about 0.03 µg/ml, at least about 0.05 µg/ml, at least about 0.07 µg/ml dexamethasone may be maintained for an extended period of time (e.g., at least about three weeks.) The preferred concentration levels of drug in the vitreous may vary according to the inflammatory mediated condition being treated. For treating uveitis, a concentration equivalent of at least about 0.01 to 0.1 µg/ml dexamethasone is preferred.

In one embodiment, said concentration is maintained for least about four weeks. In other embodiments, said concentration is maintained for at least about five weeks, at least about six weeks, at least about seven weeks, at least about eight weeks, at least about nine weeks, at least about 10 weeks, at least about 12 weeks. The preferred duration of drug release may be determined by the inflammatory mediated condition being treated. For treating uveitis, a drug release duration of at least about three weeks is preferable, more preferably at least about four weeks. In one embodiment, more than one implant may be sequentially implanted into the vitreous in order to maintain drug concentrations for even longer periods.

The implants may be inserted into the eye by a variety of methods, including placement by forceps or by trocar following making a 2-3 mm incision in the sclera. The method of placement may influence the drug release kinetics. For example, implanting the device with a trocar may result in placement of the device deeper within the vitreous than placement by forceps, which may result in the implant being closer to the edge of the vitreous. The location of the implanted device may influence the concentration gradients of drug surrounding the device, and thus influence the release rates (e.g., a device placed closer to the edge of the vitreous will result in a slower release rate).

Implants for Use in Treating Inflammatory-Mediated Conditions

The formulation of the implants for use in the invention may vary according to the preferred drug release profile, the particular glucocorticoid used, the condition being treated, and the medical history of the patient.

The implants of the invention are formulated with particles of the steroidal anti-inflammatory agent entrapped within the bioerodible polymer matrix. Release of the agent is achieved by erosion of the polymer followed by exposure of previously entrapped agent particles to the vitreous, and subsequent dissolution and release of agent. The release kinetics achieved by this form of drug release are different than that achieved through formulations which release drug through polymer swelling, such as with hydrogels such as methylcellulose. In that case, the drug is not released through polymer erosion, but through polymer swelling, which releases drug as liquid diffuses through the pathways exposed. The parameters which determine the release kinetics include the size of the drug particles, the water solubility of the drug, the ratio of drug to polymer, the method of manufacture, the surface area exposed, and the erosion rate of the polymer.

Preferably, the steroidal anti-inflammatory agent is selected from the group consisting of 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide. In a preferred embodiment, the steroidal anti-inflammatory agent is selected from the group consisting of cortisone, dexamethasone, hydrocortisone, methylprednisolone, prednisolone, prednisone, and triamcinolone. In a more preferred embodiment, the steroidal anti-inflammatory agent is dexamethasone. In another embodiment, the bioerodible implant comprises more than one steroidal anti-inflammatory agent.

The implants may further comprise one or more additional therapeutic agents, such as antimetabolites and/or antibiotics. Antimetabolites include, but are not limited to, folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thioguanine), and pyrimidine analogs (e.g., ancitabine, azacitidine, 6-azauridine, carmofur, cytarabine, doxifluridine, emitefur, enocitabine, floxuridine, fluorouracil, gemcitabine, tegafur). Specific antibiotics include, but are not limited to:

Antibacterial Antibiotics:

Aminoglycosides (e.g., amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (e.g., azidamfenicol, chloramphenicol, florfenicol, thiamphenicol), ansamycins (e.g., rifamide, rifampin, rifamycin sv, rifapentine, rifaximin), β-lactams (e.g., carbacephems (e.g., loracarbef), carbapenems (e.g., biapenem, imipenem, meropenem, panipenem), cephalosporins (e.g., cefaclor, cefadroxil, cefamandole, cefatrizine, cefazedone, cefazolin, cefcapene pivoxil, cefclidin, cefdinir, cefditoren, cefepime, cefetamet, cefixime, cefmenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (e.g., cefbuperazone, cefinetazole, cefminox, cefotetan, cefoxitin), monobactams (e.g., aztreonam, carumonam, tigemonam), oxacephems, flomoxef, moxalactam), penicillins (e.g., amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin g benethamine, penicillin g benzathine, penicillin g benzhydrylamine, penicillin g calcium, penicillin g hydrabamine, penicillin g potassium, penicillin g procaine, penicillin n, penicillin o, penicillin v, penicillin v benzathine, penicillin v hydrabamine, penimepicycline, phenethicillin potassium, piperacillin, pivampicillin, propicillin, quinacillin, sulbenicillin, sultamicillin, talampicillin, temocillin, ticarcillin), other (e.g., ritipenem), lincosamides (e.g., clindamycin, lincomycin), macrolides (e.g., azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (e.g., amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (e.g., apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin).

Synthetic Antibacterials:

2,4-Diaminopyrimidines (e.g., brodimoprim, tetroxoprim, trimethoprim), nitrofurans (e.g., furaltadone, furazolium chloride, nifuradene, nifuratel, nifurfoline, nifurpirinol, nifurprazine, nifurtoinol, nitrofurantoin), quinolones and analogs (e.g., cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (e.g., acetyl sulfamethoxypyrazine, benzylsulfamide, chloramine-b, chloramine-t, dichloramine t, $n^2$-formylsulfisomidine, $n^4$-β-d-glucosylsulfanilamide, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachloropyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, 4-sulfanilamidosalicylic acid, $n^4$-sulfanilylsulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (e.g., acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (e.g., clofoctol, hexedine, methenamine, methenamine anhydromethylene-citrate, methenamine hippurate, methenamine mandelate, methenamine sulfosalicylate, nitroxoline, taurolidine, xibornol).

Antifungal Antibiotics:

Polyenes (e.g., amphotericin b, candicidin, dermostatin, filipin, fungichromin, hachimycin, hamycin, lucensomycin, mepartricin, natamycin, nystatin, pecilocin, perimycin), others (e.g., azaserine, griseofulvin, oligomycins, neomycin undecylenate, pyrrolnitrin, siccanin, tubercidin, viridin).

Synthetic Antifungals:

Allylamines (e.g., butenafine, naftifine, terbinafine), imidazoles (e.g., bifonazole, butoconazole, chlordantoin, chlormidazole, cloconazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (e.g., tolciclate, tolindate, tolnaftate), triazoles (e.g., fluconazole, itraconazole, saperconazole, terconazole) others (e.g., acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, zinc propionate).

Antineoplastic:

Antibiotics and analogs (e.g., aclacinomycins, actinomycin $f_1$, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, zorubicin), antimetabolites (e.g. folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thioguanine), pyrimidine analogs (e.g., ancitabine, azacitidine, 6-azauridine, carmofur, cytarabine, doxifluridine, emitefur, enocitabine, floxuridine, fluorouracil, gemcitabine, tegafur).

The steroidal anti-inflammatory agent is preferably from about 10 to 90% by weight of the implant. More preferably, the agent is from about 50 to about 80% by weight of the implant. In a preferred embodiment, the agent comprises about 50% by weight of the implant. In a particularly preferred embodiment, the agent comprises about 70% by weight of the implant.

The implants are preferably monolithic, i.e. having the glucocorticoid homogenously distributed through the polymeric matrix. The selection of the polymeric composition to be employed will vary with the desired release kinetics, patient tolerance, the nature of the disease to be treated and the like. Characteristics of the polymers will include biodegradability at the site of implantation, compatibility with the agent of interest, ease of encapsulation, water insolubility, and the like. Preferably, the polymeric matrix will not be fully degraded until the drug load has been released. The polymer will usually comprise at least about 10, more usually at least about 20 weight percent of the implant.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked, usually not more than lightly cross-linked, generally less than 5%, usually less than 1%. For the most part, besides carbon and hydrogen, the polymers will include oxygen and nitrogen, particularly oxygen. The oxygen may be present as oxy, e.g., hydroxy or ether, carbonyl, e.g., non-oxocarbonyl, such as carboxylic acid ester, and the like. The nitrogen may be present as amide, cyano and amino The biodegradable polymers set forth in Heller, Biodegradable Polymers in Controlled Drug Delivery, in: CRC Critical Reviews in Therapeutic Drug Carrier Systems, Vol. 1. CRC Press, Boca Raton, Fla. (1987), may be used.

Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The % of polylactic acid in the polylactic acid polyglycolic acid (PLGA) copolymer can be 0-100%, preferably about 15-85%, more preferably about 35-65%. In a particularly preferred embodiment, a 50/50 PLGA copolymer is used. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. The size of the polymer particles is preferably about 1-100 µm in diameter, more preferably about 5-50 µm in diameter, more preferably about 9-12 µm in diameter, still more preferably about 10 µm in diameter.

Among the polysaccharides of interest are calcium alginate, and functionalized celluloses, particularly carboxymethylcellulose esters characterized by being biodegradable, water insoluble, a molecular weight of about 5 kD to 500 kD, etc.

Additionally, release modulators such as those described in U.S. Pat. No. 5,869,079 may be included in the implants. The amount of release modulator employed will be dependent on the desired release profile, the activity of the modulator, and on the release profile of the glucocorticoid in the absence of modulator.

Other agents may be employed in the formulation for a variety of purposes. For example, buffering agents and preservatives may be employed. Water soluble preservatives which may be employed include sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol. These agents may be present in individual amounts of from about 0.001 to about 5% by weight and preferably about 0.01 to about 2%. Suitable water soluble buffering agents that may be employed are sodium carbonate, sodium borate, sodium phosphate, sodium acetate, sodium bicarbonate, etc., as approved by the FDA for the desired route of administration. These agents may be present in amounts sufficient to maintain a pH of the system of between 2 to 9 and preferably 4 to 8. As such the buffering agent may be as much as 5% on a weight to weight basis of the total composition. Electrolytes such as sodium chloride and potassium chloride may also be included in the formulation. Where the buffering agent or enhancer is hydrophilic, it may also act as a release accelerator. Hydrophilic additives act to increase the release rates through faster dissolution of the material surrounding the drug particles, which increases the surface area of the drug exposed, thereby increasing the rate of drug bioerosion. Similarly, a hydrophobic buffering agent or enhancer dissolve more slowly, slowing the exposure of drug particles, and thereby slowing the rate of drug bioerosion.

The proportions of glucocorticoid, polymer, and any other modifiers may be empirically determined by formulating several implants with varying proportions. A USP approved method for dissolution or release test can be used to measure the rate of release (USP 23; NF 18 (1995) pp. 1790-1798). For example, using the infinite sink method, a weighed sample of the drug delivery device is added to a measured volume of a solution containing 0.9% NaCl in water, where the solution volume will be such that the drug concentration is after release is less than 5% of saturation. The mixture is maintained at 37° C. and stirred slowly to maintain the implants in suspension. The appearance of the dissolved drug as a function of time may be followed by various methods known in the art, such as spectrophotometrically, HPLC, mass spectroscopy, etc. until the absorbance becomes constant or until greater than 90% of the drug has been released.

The release kinetics of the drug delivery devices of the invention are dependent in part on the surface area of the devices. Larger surface area exposes more polymer to the vitreous, causing faster erosion and dissolution of the drug particles entrapped by the polymer. The size and form of the implant can be used to control the rate of release, period of treatment, and drug concentration at the site of implantation. Larger implants will deliver a proportionately larger dose, but depending on the surface to mass ratio, may have a slower release rate. The implants may be particles, sheets, patches, plaques, films, discs, fibers, microcapsules and the like and may be of any size or shape compatible with the selected site of insertion, as long as the implants have the desired release kinetics. Preferably, the implant to be inserted is formulated as a single particle. Preferably, the implant will not migrate from the insertion site following implantation. The upper limit for the implant size will be determined by factors such as the desired release kinetics, toleration for the implant, size limitations on insertion, ease of handling, etc. The vitreous chamber is able to accommodate relatively large implants of varying geometries, having diameters of 1 to 3 mm. In a preferred embodiment, the implant is a cylindrical pellet (e.g., rod) with dimensions of about 2 mm×0.75 mm diameter. The implants will also preferably be at least somewhat flexible so as to facilitate both insertion of the implant in the vitreous and accommodation of the implant. The total weight of the implant is preferably about 250-5000 µg, more preferably about 500-1000 µg. In one embodiment, the implant is about 500 µg. In a particularly preferred embodiment, the implant is about 1000 µg.

In a preferred embodiment, a solid bioerodible implant for treating an inflammation-mediated condition of the eye is provided, consisting essentially of: dexamethasone particles entrapped within a polylactic acid polyglycolic acid (PLGA) copolymer, wherein the implant comprises about 70 percent by weight of dexamethasone and about 30 percent by weight of PLGA, wherein the total mass of the implant is about 800-1100 µg, and wherein the implant releases at least about 10% of the drug load within 1 week when measured under infinite sink conditions in vitro. In a more preferred embodiment, the total mass of the implant is about 1000 µg. In other embodiments, the implant releases at least about 15%, at least about 20%, at least about 25%, at least about 30%, at least about 35%, of the drug load within 1 week when measured under infinite sink conditions in vitro. In other embodiments, the implant releases at least about 15%, at least about 20%, at least about 30%, at least about 40%, at least about 50%, of the drug load within 2 weeks when measured under infinite sink conditions in vitro.

Methods for Making the Implants of the Invention

Various techniques may be employed to produce the implants. Useful techniques include phase separation methods, interfacial methods, extrusion methods, compression methods, molding methods, injection molding methods, heat press methods and the like.

Choice of the technique, and manipulation of the technique parameters employed to produce the implants can influence the release rates of the drug. Room temperature compression methods result in an implant with discrete microparticles of drug and polymer interspersed. Extrusion methods result in implants with a progressively more homogenous dispersion of the drug within the polymer, as the production temperature is increased. When using extrusion methods, the polymer and drug are chosen to as to be stable at the temperatures required for manufacturing, usually at least about 85° C. Extrusion methods use temperatures of about 25° C. to about 150° C., more preferably about 65° C. to about 130° C. Generally, compression methods yield implants with faster release rates than extrusion methods, and higher temperatures yield implants with slower release rates.

In a preferred embodiment, compression methods are used to produce the implants of the invention. Preferably, compression methods use pressures of 50-150 psi, more preferably about 70-80 psi, even more preferably about 76 psi, and use temperatures of about 0° C. to about 115° C., more preferably about 25° C. In another preferred embodiment, extrusion methods are used. Preferably, implants produced by extrusion methods are heated to a temperature range of about 60° C. to about 150° C. for drug/polymer mixing, more preferably about 130° C., for a time period of about 0 to 1 hour, 0 to 30 minutes, 5-15 minutes, preferably about 10 minutes, preferably about 0 to 5 min. Preferably, the implants are then extruded at a temperature of about 60° C. to about 130° C., more preferably about 75° C.

Kits for the Administration of the Implants

In another aspect of the invention, kits for treating an inflammation-mediated condition of the eye are provided, comprising: a) a container comprising a bioerodible implant comprising dexamethasone and polylactic acid polyglycolic acid (PLGA) copolymer in a ratio of about 70/30; and b) instructions for use.

The invention is further illustrated by the following non-limiting examples.

EXAMPLES

Example 1

Manufacture and In Vitro Testing of Bioerodible Dexamethasone Posterior Segment Drug Delivery System (DEX PS DDS®)

2100 mg of dexamethasone powder (Upjohn) (particle sizes less than 10 µm in diameter) were mixed with 900 mg of 50/50 polylactic acid polyglycolic acid (PLGA) (particle sizes approximately 9-12 µm in diameter) at ambient temperature. A small Teflon® tube was filled with 900-1100 μg of the above mixture, and placed directly on the die cavity. The powder was pushed out of the tubing into the die cavity with a stainless steel wire and the tube and wire were removed from the die. The powder was pressed using a tablet press (approximately 76 psi), ejected with the ejector switch, and removed with tweezers. The resulting pellet was approximately 2 mm×0.75 mm.

Release of dexamethasone from the DEX PS DDS® system was measured. One DDS was placed in a glass vial filled with receptor medium (0.9% NaCl in water). To allow for "infinite sink" conditions, the receptor medium volume was chosen so that the concentration would never exceed 5% of saturation. To minimize secondary transport phenomena, e.g. concentration polarization in the stagnant boundary layer, the glass vial was placed into a shaking water bath at 37° C. Samples were taken for HPLC analysis from the vial at defined time points. The HPLC method was as described in USP 23 (1995) pp. 1791-1798. The concentration values were used to calculate the cumulative release data, as shown in Table 1.

TABLE 1

| DEX PS DDS ® In vitro Release | |
|---|---|
| Day | % Total Release |
| 1 | 10.1 |
| 2 | 16.4 |
| 7 | 39.4 |
| 14 | 55.5 |
| 21 | 69.3 |
| 28 | 80.7 |
| 35 | 88.1 |

Table 1 shows an almost linear in vitro release of dexamethasone over a one month period of time.

Example 2

In Vivo Testing of DEX PS DDS® in Rabbits

One DEX PS DDS® per eye was implanted into the vitreous of four rabbits with forceps. The in vivo vitreous concentrations of dexamethasone in each of the four eyes were monitored by vitreous sampling. For example, at day 2 the concentrations measured were 0.03 μg/ml, 0.1 μg/ml, 0.33 μg/ml and 0.19 μg/ml. The concentrations in each of the four eyes were measured on days 2, 7, 21, 28 and 35; the average results are summarized in Table 2. The volume of rabbit eyes is approximately 60-70% percent that of human eyes.

TABLE 2

| In vivo concentrations of dexamethasone (DDS placed with forceps) | |
|---|---|
| Day | μg/ml |
| 2 | 0.16 ± 0.13 |
| 7 | 0.15 ± 0.16 |
| 21 | 0.08 ± 0.07 |
| 28 | 0.005 ± 0.01 |
| 35 | 0.037 ± 0.03 |

The same DDS was tested in vivo in rabbits, wherein the DDS was placed to a depth of about 5-10 mm in the vitreous with trocar. The levels of dexamethasone in the vitreous are shown in Table 3.

TABLE 3

| In vivo concentrations of dexamethasone (DDS placed with trocar) | | | | | | | | | | |
|---|---|---|---|---|---|---|---|---|---|---|
| | Sample ID | | | | | | | | | |
| Hours | 5293-D | 5295-D | 5293-S | 5295-S | 5304-D | 5306-D | 5304-S | 5306-S | Avg | SD |
| | Sample Conc., ug/ml | | | | | | | | | |
| 2 | 0.56 | 3.07 | | | | | | | 1.82 | 1.77 |
| 4 | | | 5.48 | 6.95 | | | | | 6.22 | 1.04 |
| 6 | | | | | 2.08 | 5.15 | | | 3.62 | 2.17 |
| 24 | | | | | | | 2.33 | 2.69 | 2.51 | 0.25 |

| | DDS wt. | Dex wt. | Dex ug/mL | | | | | |
|---|---|---|---|---|---|---|---|---|
| Animal#\day | ug | ug | 2 | 7 | 14 | 21 | 28 | 35 |
| 21427-D | 990 | 693 | 2.29 | | | | | |
| 21427-S | 1023 | 715.1 | 1.56 | | | | | |
| 21433-D | 804 | 562.8 | 1.2 | | | | | |
| 21433-S | 1057 | 739.9 | 0.77 | | | | | |
| 21428-D | 1003 | 702.1 | | 9.26 | | | | |
| 21428-S | 1025 | 717.5 | | 0.35 | | | | |
| 21434-D | 863 | 604.1 | | 3.31 | | | | |
| 21434-S | 1106 | 774.2 | | 0.84 | | | | |
| 21429-D | 1013 | 709.1 | | | n/a | | | |
| 21429-S | 927 | 648.9 | | | 0.19 | | | |
| 21435-D | 1104 | 772.8 | | | 0.43 | | | |
| 21435-S | 941 | 658.7 | | | 0.11 | | | |
| 21432-D | 860 | 692 | | | | 0.43 | | |
| 21432-S | 941 | 685.7 | | | | 1.72 | | |
| 21436-D | 1010 | 707 | | | | 0.31 | | |
| 21436-S | 1054 | 737.8 | | | | 0.13 | | |
| 21431-D | 996 | 697.2 | | | | | 0.52 | |
| 21431-S | 918 | 642.6 | | | | | 1.15 | |
| 21437-D | 1049 | 732.9 | | | | | 0.19 | |
| 21437-D | 1075 | 752.5 | | | | | 0.48 | |

TABLE 3-continued

In vivo concentrations of dexamethasone (DDS placed with trocar)

| | | | | | | | | |
|---|---|---|---|---|---|---|---|---|
| 21430-D | 994 | 695.8 | | | | | | 0.06 |
| 21430-S | 1086 | 760.2 | | | | | | 0.18 |
| 21438-D | 974 | 681.8 | | | | | | 0.03 |
| 21438-S | 831 | 581.7 | | | | | | 8.35 |
| Ave. | 985.17 | 694.43 | 1.46 | 3.44 | 0.24 | 0.65 | 0.59 | 2.16 |

\* Unable to determine due to insufficient sample

The data indicate that the DEX PS DDS® releases dexamethasone to the vitreous in concentrations above 0.01 μg/ml for an extended period of time. Further, the data indicate that placement of the device with trocar results in much higher levels of drug release than with placement with forceps, most likely due to placement of the device deeper within the vitreous. The data at two, four, six, and 24 hours in Table 3 shows an initial spike of drug release.

Example 3

Treatment of Severe Uveitis in Human Patients with DEX PS DDS®

Three eyes of two patients (ages 5 and 55 years) with severe progressive uveitis were treated with the DEX PS DDS®. The use of the DEX PS DDS® in compassionate and emergency use situations was conducted under an investigative new drug application (IND) with the U.S. F.D.A. A written informed consent was obtained from the participating patients.

Subjects in this study underwent pars plana vitrectomy. Immediately after the vitrectomy, the DEX PS DDS® was inserted into the vitreous cavity through the pars plana. The DDS pellet appeared to remain in the location where it was placed, and released the drug over at least approximately 4-5 weeks.

Patient #1 was a 55-year-old female who initially presented with optic neuritis in 1990. This patient subsequently developed recurrent posterior uveitis secondary to inflammatory polyarthritis. Response to systemic and periocular steroid treatment was intermittent. Methotrexate and cyclosporine were found to be effective; however, these drugs induced severe side effects. Methotrexate caused elevated liver enzymes and pancreatitis. The patient developed pustular dermatitis with cyclosporine treatment. Cytoxan was subsequently used, both intravenously and orally, with satisfactory initial results. Later, the inflammatory polyarthritis was controlled with Gold injections. The patient's Type I diabetes was well controlled and the pancreatitis resolved.

The patient was referred to us in September 1998 for further evaluation and treatment of uveitis due to progressive visual loss and lack of response to conventional medications. A vitrectomy had been performed on her left eye several years earlier for treatment of uveitis. Visual acuity in both eyes was counting fingers. Intraocular pressure in both eyes was 20 mm Hg. Slit lamp exam of the right anterior chamber revealed trace flare and 1-5 cells. Examination of the left anterior chamber revealed no flare and 8-9 cells. A mild nuclear sclerotic cataract was present in the right eye and a moderate one was noted in the left eye. In the anterior vitreous of the right eye, 50-100 fine cells were present. There were 6-7 cells in the left anterior vitreous.

On ophthalmoscopy of the right eye, the vitreous was hazy and a poor view was obtained. It was possible to see a peripapillary scar and numerous histoplasmosis type retinal scars 360° from the posterior pole out to the periphery. In the left eye, the vitreous was not as hazy and the retina appearance was very similar to that of the right eye. The right eye was selected for initial treatment due to its more acute involvement and the more severe inflammatory response.

In October 1998, a standard three port system pars plana vitrectomy was performed and the DEX PS DDS® was inserted through the pars plana. At the end of surgery, the patient received periocular celestone suspension 1 cc (β-methasone sodium phosphate/(β-methasone acetate, Schering-Plough) and periocular gentamicin 0.1 cc (Abbott Laboratories). Topical medications consisting of Tobradex® (tobramycin/dexamethasone, Alcon Labs) and Cyclogyl® 1% drops (cyclopentolate HCl, Alcon Labs) q.i.d. were prescribed. The retina was clearly seen for the first time during surgery after removal of the vitreous. There was a peripapillary scar and numerous healed histoplasmosis type scars 360° from the posterior pole to the periphery. In addition, there were several small retinal hemorrhages that appeared to be consistent with diabetic retinopathy. No active inflammatory retinitis or choroiditis was seen. A mild amount of epiretinal gliosis was present at six o'clock in the mid-periphery. There was no evidence of snowbanking or snowball opacities.

The first (right) eye of patient #1 improved from counting fingers to 20/200 on the first day postoperatively. The best vision was 20/40 at six months. One year acuity was 20/50 and at the last visit (16 months) the vision was 20/60 (Table 3).

TABLE 4

Patient 1: Right Eye Visual Acuity

| | Visual Acuity |
|---|---|
| PreOp | CF |
| Day 1 | 20/200 |
| Month 1 | 20/200 |
| Month 2 | 20/80 |
| Month 3 | 20/60 |
| Month 4 | 20/40 |
| Month 5 | 20/50 |
| Month 16 | 20/60 |

Postoperatively, anterior chamber flare varied between 0 and trace and cells varied between 1 and 6. Vitreous flare varied between 0 and trace. Vitreous cells varied between 0 and 20.

On ophthalmoscopy, the vitreous and retina were found to remain completely quiet. The DEX PS DDS® implant was resorbed at approximately five weeks. The retinal hemorrhages disappeared. There was no detectable increase in the patient's cataract. Fluorescein angiography did not reveal any evidence of macular edema. Present eye medications consist of Acular® (ketorolac promethamine 0.5%, Allergan) drops q.i.d.

After it was determined that favorable results were achieved in the right eye, the patient received the same treatment for the left eye in April 1999. The left eye presented very similarly to the right eye, other than a more significant cataract and the uveitis being more chronic in nature. Notably, a pars plana vitrectomy had been performed on this eye for this condition 3 years previously.

The second (left) eye of patient #1 initially improved to a visual acuity of 20/400 (3 months postoperatively), but later returned to counting fingers (7.5 months). This decline in visual acuity appeared to be secondary to progression of the cataract. Postoperatively (first 10 months), on slit lamp examination, anterior chamber flare varied from 0 to moderate and cells varied from 0 to >30. Vitreous flare varied from 0 to severe and vitreous cells varied from 0 to >250. On the last visit (11 months), there was no AC flare or cells, and vitreous detail was not observed due to cataract. There had been no vitreous flare or cells detected on the previous visit (10 months). Visual acuity at 11 months was counting fingers. Present eye medications consist of Acular® drops q.i.d.

Patient #2 is a 5-year-old male with an eight month history of bilateral pars planitis. The right eye was mild and stable, but the left eye was progressive and severe with only transient response to topical and subtenon steroids. This was an idiopathic uveitis. The patient developed complications in the left eye including decreased vision to 20/200, a posterior subcapsular cataract, band keratopathy, and glaucoma with intraocular pressures in the low 30's. There was mild flare and 20 cells in the anterior chamber.

The anterior vitreous was very prominent and the cells were too numerous to count. On ophthalmoscopy, the patient was found to have snowball vitreous opacities, snowbanking, and peripheral retinoschisis or a low retinal detachment. Multiple uveitis consultations offered treatment choices of systemic steroids, systemic antimetabolites, and pars plana vitrectomy. Because of the patient's young age and potential side effects of systemic treatments, it was elected to perform a pars plana vitrectomy. The surgery was carried out uneventfully in September 1999. The treatment consisted of a pars plana vitrectomy, insertion of DEX PS DDS®, and transconjunctival cryopexy.

Patient #2 had a one day postoperative visual acuity of 20/400 and the best vision was 20/70 (Table 4).

TABLE 5

Patient 2: Left Eye Visual Acuity

|  | Visual Acuity |
| --- | --- |
| PreOp | 20/200 |
| Month 1 | 20/70 |
| Month 2 | 20/100 |
| Month 3 | 20/70 |
| Month 4 | 20/80 |
| Month 5 | 20/100 |
| Month 6 | 20/80 |

Visual acuity at five months decreased to 20/100 secondary to progression of the posterior subcapsular cataract. On slit lamp examination, anterior chamber flare varied between 0 to mild and cells varied from 0 to 4. Vitreous flare was 0 and vitreous cells varied from 0 to 10. On ophthalmoscopy, a mild amount of residual snowballs and snowbanking was evident. The peripheral retinal detachment/schisis healed well and was flat. The eye responded very well with the exception of intraocular pressure. Pressures were in the teens up to the 20's in the immediate postoperative period, and after two months the pressure went up to 44 mm Hg. A glaucoma consultation was obtained and it was concluded that the intraocular pressure increase was due to the topical antibiotic steroid combination drops used postoperatively. The medications were terminated and the patient was prescribed topical anti-glaucoma medication. The last postoperative pressure measurement (6 months) was 13 mm Hg. There is no evidence of damage to the optic nerve. Present medications consist of Timoptic® 0.25% (timolol maleate, Falcon Pharmaceuticals), Acular®, and Vexol® 1% (rimexolone, Alcon Labs) all b.i.d.

Outcomes for these two patients suggest that DEX PS DDS® may be very effective in the treatment of severe uveitis. It appears that the DEX PS DDS® is well tolerated, and that the one month drug delivery system can be effective over a much longer period of time in treating these chronic uveitis patients.

Example 4

Treatment of Severe and Recalcitrant Uveitis in Human Patients with DEX PS DDS®

Four eyes of 4 patients who have had failed treatments for severe uveitis were treated with the DEX PS DDS®. Subjects in this study underwent a standard 3 port pars plana vitrectomy Immediately after the vitrectomy, the DEX PS DDS® was inserted into the vitreous cavity through the pars plana. The DDS pellet appeared to remain in the location where it was placed, and released the drug over approximately 1 month.

Three patients had a single procedure with DEX PS DDS® insertion and 1 patient had a second DEX PS DDS® insertion when surgery was required from complications of the disease. All patients have shown a remarkable response to the medication and vision in all patients has improved. The beginning vision was as low as counting fingers only and the improvement has been as high as 20/30. With 2-22 months follow up all patients have responded positively and there have been no new recurrences. The patient who had 2 insertions has shown complete regression of the disease.

Example 5

Use of DEX PS DDS® in the Treatment of Recurrent Retinal Detachment

The effect of DEX PS DDS® as an adjunct in the treatment of recurrent retinal detachments associated with PVR was evaluated. Six eyes of six patients with 2-4 previous retinal procedures and who had recurrence due to PVR were treated with DEX PS DDS®, which was inserted into the vitreous cavity after a standard 3 port pars plana vitrectomy with membrane peeling, endolaser, and air-fluid-gas or silicone oil exchange, with or without a scleral buckle.

Four patients had surgery with reattachment with one operation. Two patients had a second procedure due to initial incomplete removal of the existing PVR. With the second procedure the retina of one patient has remained attached. The second patient has developed recurrent PVR and re-detachment and will undergo further surgery. With 3-13 months follow-up five retinas were attached with no new PVR.

The DEX PS DDS® appeared to be very effective in the treatment of PVR related retinal detachments.

Example 6

Manufacture and In Vitro Testing of 50/50 Dexamethasone/PLGA Posterior Segment Drug Delivery System 2.5 g of PLGA (particle sizes approximately 9-12 μm in diameter) were placed in a mixing vessel. The vessel was placed in the oven (130° C.) for ten minutes. 2.5 g of dexamethasone (particle sizes less than approximately 10 μm in diameter) were added to the vessel, and the vessel was returned to the oven for 10 minutes. The PLGA/dexamethasone mixture was mixed well, the blend loaded into a barrel, and 650-790 μm diameter filaments extruded. The resulting filaments were cut into lengths of approximately 0.94 and 1.87 mm for the 500 μg and 1000 μg formulations, respectively.

Release of dexamethasone from the 50/50 dexamethasone/PLGA DDS formulations were measured. One DDS was placed in a glass vial filled with receptor medium (0.9% NaCl in water). To allow for "infinite sink" conditions, the receptor medium volume was chosen so that the concentration would never exceed 5% of saturation. To minimize secondary transport phenomena, e.g. concentration polarization in the stagnant boundary layer, the glass vial was placed into a shaking water bath at 37° C. Samples were taken for HPLC analysis from the vial at defined time points. The HPLC method was as described in USP 23 (1995) pp. 1791-1798. The concentration values were used to calculate the cumulative release data, as shown in Table 6.

TABLE 6

In vitro release of 50% Dex-PS (0.5 mg formulation)

| Day | Dex ug Release/day | % Total release |
|---|---|---|
| 50% Dex PS 0.5 mg system replicate 1 | | |
| 1 | 3.00 | 1.41 |
| 7 | 1.99 | 7.93 |
| 13 | 0.90 | 13.43 |
| 20 | 1.79 | 30.21 |
| 27 | 1.54 | 49.77 |
| 34 | 1.93 | 80.52 |
| 41 | 0.24 | 85.05 |
| 48 | 0.24 | 90.38 |
| 55 | 0.10 | 93.00 |
| 62 | 0.15 | 97.44 |
| 69 | 0.07 | 99.84 |
| 76 | 0.07 | 102.25 |
| 50% Dex PS 0.5 mg system replicate 2 | | |
| 1 | 6.00 | 2.17 |
| 7 | 1.66 | 6.38 |
| 13 | 0.99 | 11.05 |
| 20 | 1.21 | 19.82 |
| 27 | 2.29 | 42.23 |
| 34 | 2.34 | 71.05 |
| 41 | 0.44 | 77.54 |
| 48 | 0.29 | 82.61 |
| 55 | 0.14 | 85.34 |
| 62 | 0.20 | 89.80 |
| 69 | 0.10 | 92.21 |
| 76 | 0.06 | 84.38 |
| 50% Dex PS 0.5 mg system replicate 3 | | |
| 1 | 5.70 | 3.27 |
| 7 | 1.11 | 7.71 |
| 13 | 0.83 | 13.83 |
| 20 | 0.05 | 14.47 |
| 27 | 1.63 | 39.63 |
| 34 | 1.52 | 69.26 |
| 41 | 0.21 | 74.10 |
| 48 | 0.19 | 79.23 |
| 55 | 0.08 | 81.69 |
| 62 | 0.14 | 86.58 |
| 69 | 0.07 | 89.46 |
| 76 | 0.06 | 92.26 |

TABLE 7

In vitro release of 50% Dex-PS (1 mg formulation)

| Day | Dex ug Release/day | % Total release |
|---|---|---|
| 50% Dex PS 1 mg system replicate 1 | | |
| 1 | 6.90 | 1.28 |
| 7 | 3.48 | 5.78 |
| 13 | 1.93 | 10.43 |
| 20 | 3.46 | 23.22 |
| 27 | 3.74 | 41.89 |
| 34 | 3.94 | 66.83 |
| 41 | 1.79 | 80.17 |
| 48 | 1.28 | 91.49 |
| 55 | 0.21 | 93.59 |
| 62 | 0.24 | 96.39 |
| 69 | 0.11 | 97.85 |
| 76 | 0.09 | 99.11 |
| 50% Dex PS 1 mg system replicate 2 | | |
| 1 | 3.90 | 0.71 |
| 7 | 2.26 | 3.62 |
| 13 | 1.66 | 7.57 |
| 20 | 3.14 | 19.09 |
| 27 | 4.32 | 40.48 |
| 34 | 4.06 | 65.77 |
| 41 | 1.61 | 77.90 |
| 48 | 1.34 | 89.70 |
| 55 | 0.19 | 91.60 |
| 62 | 0.23 | 94.18 |
| 69 | 0.10 | 95.50 |
| 76 | 0.09 | 96.78 |
| 50% Dex PS 1 mg system replicate 3 | | |
| 1 | 4.50 | 0.91 |
| 7 | 2.16 | 3.98 |
| 13 | 1.69 | 8.42 |
| 20 | 1.25 | 13.48 |
| 27 | 3.88 | 34.67 |
| 34 | 3.53 | 58.97 |
| 41 | 1.85 | 74.28 |
| 48 | 0.88 | 82.85 |
| 55 | 0.19 | 84.94 |
| 62 | 0.26 | 88.15 |
| 69 | 0.11 | 89.75 |
| 76 | 0.10 | 91.26 |

Example 7

In Vivo Testing of 50/50 Dexamethasone/PLGA 1 Mg Formulations in Rabbits

One 50/50 dexamethasone/PLGA 1 mg formulation DDS per eye was implanted into the vitreous of 6 rabbits using a trocar. The DDS was loaded into the trocar, a hole was punched through the sclera, the trocar inserted through the hole, and the trocar plunger depressed to insert the DDS into the vitreous. In vivo vitreous concentrations of dexamethasone were monitored, as shown in Table 8.

TABLE 8

In vivo vitreous concentrations of dexamethasone

| Hours | 5293-D | 5295-D | 5293-S | 5295-S | 5304-D | 5306-D | 5304-S | 5306-S | Avg | SD |
|---|---|---|---|---|---|---|---|---|---|---|
| | | | | Sample Conc., ug/ml | | | | | | |
| 2 | 1.38 | 1.69 | | | | | | | 1.54 | 0.22 |
| 4 | | | 2.16 | 0.96 | | | | | 0.47 | 0.37 |
| 6 | | | | | 0.73 | 0.21 | | | 0.47 | 0.37 |
| 24 | | | | | | | 0.57 | 0.74 | 0.66 | 0.12 |

| Animal#\day | 7 | 21 | 35 | 49 | 63 |
|---|---|---|---|---|---|
| | | | Dex ug/mL | | |
| 2953-D | 0.5 | | | 0.58 | |
| 2953-S | 0.11 | | | 0.69 | |
| 2952-D | 0.13 | | | 1.2 | |
| 2952-S | 0.12 | | | 0.55 | |
| 2946-D | | 0.19 | | | 2.55 |
| 2946-S | | *3 | | | 0.14 |
| 2949-D | | *5.44 | | | 0.28 |
| 2949-S | | 0.0248 | | | 0.01 |
| 2982-D | | | 1.087 | | |
| 2982-S | | | 0.058 | | |
| 2983-D | | | 0.018 | | |
| 2983-S | | | 0.045 | | |
| Ave. | 0.22 | 2.16 | 0.30 | 0.76 | 0.75 |

* High level was due to the surgical artifact

The data indicate that the 50/50 dexamethasone/PLGA DDS releases dexamethasone to the vitreous in concentrations above 0.01 μg/ml for an extended period of time. The data at two, four, six, and 24 hours in Table 8 shows an initial spike of drug release, due to drug which is unencapsulated by the delivery system.

The 100-120 μg 50/50 PLGA/dexamethasone implant disclosed in U.S. Pat. No. 5,869,079 shows similar in vitro release kinetics to the 500 and 1000 μg 50/50 PLGA/dexamethasone implant disclosed herein. However, the previously disclosed implant would not provide drug concentrations in the vitreous at the levels described herein.

Modifications of the above described modes for carrying out the invention that are obvious to those of ordinary skill in the surgical, pharmaceutical, or related arts are intended to be within the scope of the following claims.

What is claimed is:

1. A bioerodible implant for treating an inflammation-mediated condition of the eye, the implant comprising a steroidal anti-inflammatory agent and a bioerodible polymer, the implant structured to be placed in the vitreous of the eye and deliver the agent to the vitreous in an amount sufficient to reach an in vivo concentration equivalent to at least 0.05 μg/mL dexamethasone within about 48 hours and to maintain an in vivo concentration equivalent to at least 0.03 μg/mL dexamethasone for at least about three weeks.

2. The implant of claim 1, wherein the steroidal anti-inflammatory agent is selected from the group consisting of methylprednisolone, prednisolone, prednisone, prednisolone 25-diethylamino-acetate, betamethasone, beclomethasone, triamcinolone, triamcinolone acetonide, triamcinolone benetonide, and triamcinolone hexacetonide.

3. The implant of claim 1, wherein the bioerodible polymer is a polylactic acid polyglycolic acid (PLGA) copolymer.

4. The implant of claim 1, wherein the steroidal anti-inflammatory agent comprises about 10 to 90% by weight of the implant.

5. The implant of claim 1, wherein the steroidal anti-inflammatory agent comprises about 50 to about 80% by weight of the implant.

* * * * *

UNITED STATES PATENT AND TRADEMARK OFFICE
CERTIFICATE OF CORRECTION

PATENT NO. : 8,242,099 B2
APPLICATION NO. : 13/271451
DATED : August 14, 2012
INVENTOR(S) : Vernon G. Wong et al.

It is certified that error appears in the above-identified patent and that said Letters Patent is hereby corrected as shown below:

In column 1, line 44, Delete "edulimed.htm" and insert -- edu/imed.htm --, therefor.

In column 1, line 59, Delete "edulimed.htm" and insert -- edu/imed.htm --, therefor.

In column 8, line 4, Delete "cefinetazole," and insert -- cefmetazole, --, therefor.

In column 10, line 14, Delete "amino" and Insert -- amino. --, therefor.

In column 13, line 24, Delete "DDS ®" and insert -- DDS® --, therefor.

In column 16, line 20, Delete "phosphate/(β-methasone" and insert -- phosphate/β-methasone --, therefor.

In column 16, line 63, Delete "(ketorolac promethamine" and insert -- (ketorolac tromethamine --, therefor.

In column 18, lines 20-21, Delete "vitrectomy" and insert -- vitrectomy. --, therefor.

In column 19, line 43, Delete "systemreplicate" and insert -- system replicate --, therefor.

In column 20, line 58, Delete "Mg" and insert -- mg --, therefor.

Signed and Sealed this
Twenty-third Day of October, 2012

David J. Kappos
*Director of the United States Patent and Trademark Office*